(12) United States Patent
Rybak et al.

(10) Patent No.: US 7,470,524 B2
(45) Date of Patent: Dec. 30, 2008

(54) METHOD FOR PRODUCING L-AMINO ACIDS USING BACTERIA OF THE ENTEROBACTERIACEAE FAMILY

(75) Inventors: Konstantin Vyacheslavovich Rybak, Moscow (RU); Ekaterina Aleksandrovna Slivinskaya, Moscow (RU); Yury Ivanovich Kozlov, Moscow (RU); Tomoko Suzuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/275,264

(22) Filed: Dec. 21, 2005

(65) Prior Publication Data
US 2006/0141586 A1 Jun. 29, 2006

Related U.S. Application Data

(60) Provisional application No. 60/693,507, filed on Jun. 24, 2005.

(30) Foreign Application Priority Data
Dec. 23, 2004 (RU) ............................... 2004137719

(51) Int. Cl.
*C12P 13/04* (2006.01)
*C12P 13/24* (2006.01)
*C12P 13/22* (2006.01)
*C12P 13/14* (2006.01)
*C12N 1/20* (2006.01)
*C12N 15/74* (2006.01)
*C12N 15/00* (2006.01)

(52) U.S. Cl. ................. 435/106; 435/107; 435/108; 435/110; 435/200; 435/252.3; 435/252.33; 435/320.1; 435/471; 435/115; 435/114

(58) Field of Classification Search ................. 435/106, 435/69.1, 252.33
See application file for complete search history.

(56) References Cited

U.S. PATENT DOCUMENTS

| | | | |
|---|---|---|---|
| 6,960,455 | B2 | 11/2005 | Livshits et al. |
| 2003/0077764 | A1 | 4/2003 | Tsujimoto et al. |
| 2004/0038380 | A1 | 2/2004 | Debabov et al. |
| 2004/0132165 | A1 | 7/2004 | Akhverdian et al. |
| 2004/0229320 | A1 | 11/2004 | Stoynova et al. |
| 2004/0229321 | A1 | 11/2004 | Savrasova et al. |
| 2005/0048631 | A1 | 3/2005 | Klyachko et al. |
| 2005/0054061 | A1 | 3/2005 | Klyachko et al. |
| 2005/0124048 | A1 | 6/2005 | Akhverdian et al. |
| 2005/0176033 | A1 | 8/2005 | Klyachko et al. |
| 2005/0214911 | A1 | 9/2005 | Marchenko et al. |
| 2005/0214913 | A1 | 9/2005 | Marchenko et al. |
| 2005/0239175 | A1 | 10/2005 | Tabolina et al. |
| 2006/0030009 | A1 | 2/2006 | Livshits et al. |
| 2006/0035346 | A1 | 2/2006 | Savrasova et al. |

FOREIGN PATENT DOCUMENTS

| | | |
|---|---|---|
| EP | 0 488 424 | 6/1992 |
| EP | 0 796 912 | 9/1997 |
| EP | 1 078 989 | 2/2001 |
| EP | 1 170 358 | 1/2002 |
| EP | 1 577 396 | 9/2005 |
| WO | WO 03/004662 A2 * | 1/2003 |
| WO | WO 03/076637 A1 * | 9/2003 |

OTHER PUBLICATIONS

Daruwalla et al., Energization of the transport systems for arabinose and comparison with galactose transport in *Escherichia coli*. Biochem. J., 1981 vol. 200: 611-627.*
Maiden et al., The cloning, DNA sequence, and overexpression of the gene araE coding for arabinose-proton symport in *Escherichia coli* K 12. JBC., 1988 vol. 263 (17): 8003-8010.*
Johnson et al., In vivo induction kinetics of the arabinose promoters in *Escherichia coli*. J. Bacteriol., 1995, vol. 177 (12): 3438-3442.*
Schleif R., Regulation of the L-arabinose operon of *Escherichia coli*. TIG., 2000, vol. 16 (2): 559-565.*
Brown T., Hybridization analysis of DNA blots. Current Protocols in Moelcular Biology, Unit 2.10: 2.10.12.10.16, 1993, Published by John Wiley & Sons, USA.*
Guo et al., Protein tolerance to random amino acid change. PNAS., 2004, vol. 101: 9205-9210. Published online Jun. 14, 2004.*
Daruwalla, K. R., et al., "Energization of the transport systems for arabinose and comparison with galactose transport in *Escherichia coli*," Biochem. J. 1981;200:611-627.
Datsenko, K. A., et al., "One-step inactivation of chromosomal genes in *Escherichia coli* K-12 using PCR products," PNAS 2000;97(12):6640-6645.
Gold, L., et al., "Translational Initiation in Prokaryotes," Annual Reviews Microbiology 1981;35:365-403.
Griffith, J. K., et al., "Membrane transport proteins: implications of sequence comparisons," Current Op. Cell Biol. 1992;4(4):684-695.
Hui, A., et al., "Mutagenesis of the three bases preceding the start codon of the β-galactoside mRNA and its effect on translation in *Escherichia coli*," The EMBO Journal 1984;3(3):623-629.
Wovcha, M. G., et al., "Amplification of D-Xylose and D-Glucose Isomerase Activities in *Escherichia coli* by Gene Cloning," Appl. Environment. Microbiol. 1983;45(4):1402-1404.
International Preliminary Report on Patentability for PCT Patent App. No. PCT/JP2005/023829 (Jul. 5, 2007).
Database Geneseq [Online], "Bacterial polynucleotide #23536" retried from EBI accession No. GSN: ADT48785.
Database EMBL [Online] "Low-affinity L-arabinose transport system proton symport protein. *Shigella flexneri*" retrieved from EBI accession No. Q83QB4_SHIFL, Jun. 1, 2003.

(Continued)

*Primary Examiner*—Rebecca E. Prouty
*Assistant Examiner*—Ganapathirama Raghu
(74) *Attorney, Agent, or Firm*—Shelly Guest Cermak; Cermak Kenealy & Vaidya LLP

(57) ABSTRACT

There is disclosed a method for producing an L-amino acid, for example L-threonine, L-lysine, L-histidine, L-phenylalanine, L-arginine, L-tryptophan or L-glutamic acid, using a bacterium of the Enterobacteriaceae family, wherein the bacterium has been modified to enhance an activity of L-arabinose permease.

24 Claims, 2 Drawing Sheets

OTHER PUBLICATIONS

Database EMBL [Online] "L-arabinose isomerase. *Salmonella typhi*" retrieved from EBI accession No. Q8Z401_SALTI, Mar. 7, 2003.

Database Geneseq [Online] "*E. coli* protein #2" retrieved from EBI accession No. GSN: ADI27981 & US 2003/165891 A1, Jun. 10, 2003.

Maiden, M. C. J., et al., "The Cloning, DNA Sequence, and Overexpression of the Gene *araE* Coding for Arabinose-Proton Symport in *Escherichia coli* K-12," J. Biol. Chem. 1988;263(17):8003-8010.

Shatwell, K. P., et al., "Cloning, Sequencing, and Expression of the *araE* Gene of *Klebsiella oxytoca* 8017, Which Encodes Arabinose-$H^+$ Symport Activity," J. Bacteriol. 1995;177(18):5379-5380.

International Search Report and Written Opinion of the International Searching Authority for PCT App. No. PCT/JP2005/023829 (Apr. 19, 2006).

* cited by examiner

Figure 2.

```
AraE_Ec    -MVTINTESALTPRSLRDTRRMNMFVSVAAAVAGLLFGLDIGVIAGALPFITDHFVLTSR
AraE_Sf    -MVTINTESALTPRSLRDTRRMNMFVSVAAAVAGLLFGLDIGVIAGALPFITDHFVLTSR
AraE_St    -MVSINHDSALTPRSLRDTRRMNMFVSVSAAVAGLLFGLDIGVIAGALPFITDHFVLTSR
AraE_Ko    -MTTLSHDSTTMPRTQRDTRRMNQFVSIAAAVAGLLFGLDIGVIAGALPFITDHFVLSSR
AraE_Bs    MKNTPTQLEPNVPVTRSHSMGFVILISCAAGLGGLLYGYDTAVISGAIGFLKDLYSLSPF
            :  .. * :  .:  :   ::* :*..:.***:* * .**:**: *:.* : *:.

AraE_Ec    LQEWVVSSMMLGAAIGALFNGWLSFRLGRKYSLMAGAILFVLGSIGSAFATSVEMLIAAR
AraE_Sf    LQEWVVSSMMLGAAIGALFNGWLSFRLGRKYSLMAGAILFVLGSIGSAFATSVEMLIAAR
AraE_St    LQEWVVSSMMLGAAIGALFNGWLSFRLGRKYSLMAGAILFVLGSLGSAFASSVEVLIGAR
AraE_Ko    LQEWVVSSMMLGAAIGALFNGWLSFRLGRKYSLMVGAVLFVAGSVGSAFATSVEMLLVAR
AraE_Bs    MEGLVISSIMIGGVVGVISGFLSDRFGRRKILMTAALLFAISAIVSALSQDVSTLIIAR
           ::  **:*:*..:*. :.*:** *:*: **..*:**. .::  **:: .*. *: **

AraE_Ec    VVLGIAVGIASYTAPLYLSEMASENVRGKMISMYQLMVTLGIVLAFLSDTAFSYSG----
AraE_Sf    VVLGIAVGIASYTAPLYLSEMASENVRGKMISMYQLMVTLGIVLAFLSDTAFSYSG----
AraE_St    VILGVAVGIASYTAPLYLSEMASENVRGKMISMYQLMVTLGIVLAFLSDTAFSYSG----
AraE_Ko    IVLGVAVGIASYTAPLYLSEMASENVRGKMISMYQLMVTLGIVMAFLSDTAFSYSG----
AraE_Bs    IIGGLGIGMGSSLSVTYITEAAPPAIRGSLSSLYQLFTILGISATYFINLAVQRSGTYEW
           ::  *::*:.*  :   *::* *.  :**.: *:***:. ***   :::  :  *.. **

AraE_Ec    ----NWRAMLGVLALPAVLLIILVVFLPNSPRWLAEKGRHIEAEEVLRMLRDTSEKAREE
AraE_Sf    ----NWRAMLGVLALPAVLLIILVVFLPNSPRWLAEKGRHIEAEEVLRMLRDTSEKAREE
AraE_St    ----NWRAMLGVLALPAVLLIILVVFLPNSPRWLAQKGRHIEAEEVLRMLRDTSEKARDE
AraE_Ko    ----NWRAMLGVLALPAVVLIILVIFLPNSPRWLAEKGRHVEAEEVLRMLRDTSEKARDE
AraE_Bs    GVHTGWRWMLAYGMVPSVIFFLVLLVVPESPRWLAKAGKTNEALKILTRING-ETVAKEE
               .** **.  :*:*::::::::.:*:****** *: ** ::* :... . *::*

AraE_Ec    LNEIRESLKLKQGGWALFKINRNVRRAVFLGMLLQAMQQFTGMNIIMYYAPRIFKMAGFT
AraE_Sf    LNEIRESLKLKQGGWALFKINRNVRRAVFLGMLLQAMQQFTGMNIIMYYAPRIFKMAGFT
AraE_St    LNEIRESLKLKQGGWALFKANRNVRRAVFLGMLLQAMQQFTGMNIIMYYAPRIFKMAGFT
AraE_Ko    LNEIRESLKLKQGGWALFKVNRNVRRAVFLGMLLQAMQQFTGMNIIMYYAPRIFKMAGFT
AraE_Bs    LKNIENSLKIEQMGSLSQLFKPGLRKALVIGILLALFNQVIGMNAITYYGPEIFKMMGFG
           *::*.:***::* *    : .:*:*:..:*:** ::*. *** * **.*.**** **

AraE_Ec    TTEQQMIATLVVGLTFMFATFIAVFTVDKAGRKPALKIGFSVMALGTLVLGYCLMQFDNG
AraE_Sf    TTEQQMIATLVVGLTFMFATFIAVFTVDKAGRKPALKIGFSVMALGTLVLGYCLMQFDNG
AraE_St    TTEQQMIATLVVGLTFMFATFIAVFTVDKAGRKPALKIGFSVMALGTLVLGYCLMQFDNG
AraE_Ko    TTEQQMVATLVVGLTFMFATFIAVFTVDKAGRKPALKIGFSVMAIGTLVLGYCLMQFDNG
AraE_Bs    -QNAGFVTTCIVGVVEVIFTVIAVLLIDKVGRKKLMSIGSAFMAIFMILIG---TSFYFE
            :   :::* :**:. :: *.***: :**.*** :.** :.**:   :::*   .*

AraE_Ec    TASSGLSWLSVGMTMMCIAGYAMSAAPVVWILCSEIQPLKCRDFGITCSTTTNWVSNMII
AraE_Sf    TASSGLSWLSVGMTMMCIAGYAMSAAPVVWILCSEIQPLKCRDFGITCSTTTNWVSNMII
AraE_St    TASSGLSWLSVGMTMMCIAGYAMSAAPVVWILCSEIQPLKCRDFGITCSTTTNWVSNMII
AraE_Ko    TASSGLSWLSVGMTMMCIAGYAMSAAPVVWILCSEIQPLKCRDFGITCSTTTNWVSNMII
AraE_Bs    LTSG---IMMIVLILGFVAAFCVSVGPITWIMISEIFPNHLRARAAGIATIFLWGANWAI
           :*.     :  : : : :*.:..:*..*:.**   *** * :*  .  :*   * :* *

AraE_Ec    GATFLTLLDSIGAAGTFWLYTALNIAFVGITFWLIPETKNVTLEHIERKLMAGEKLRNIGV
AraE_Sf    GAAFLTLLDSIGAAGTFWLYTALNIAFVGITFWLIPETKNVTLEHIERKLMAGEKLRNIGV
AraE_St    GATFLTLLDSIGAAGTFWLYTALNIAFIGITFWLIPETKNVTLEHIERKLMAGEKLRNIGV
AraE_Ko    GATFLTLLDAIGAAGTFWLYTALNVAFIGVTFWLIPETKNVTLEHIERRLMSGEKLRNIGN
AraE_Bs    GQFVPMMIDSFGLAYTFWIFAVINILCFLFVVTICPETKNKSLEEIEKLWIK---------
           *   .  ::*::* *  ***:::.:*  .... : ***** :**.** :
```

METHOD FOR PRODUCING L-AMINO ACIDS USING BACTERIA OF THE ENTEROBACTERIACEAE FAMILY

This application claims priority under 35 U.S.C. §119(a) to Russian application No. 2004137719, filed on Dec. 23, 2004, and under 35 U.S.C. §119(e) to U.S. provisional application 60/693,507, filed on Jun. 24, 2005, the entireties of both of which are incorporated by reference. Also, the Sequence Listing on compact disk filed herewith is hereby incorporated by reference (File name: US-195 Seq List; File size: 14 KB; Date recorded: Dec. 20, 2005).

BACKGROUND OF THE INVENTION

1. Technical Field

The present invention relates to a method for producing an L-amino acid by fermentation, and more specifically to genes which aid in this fermentation. These genes are useful for improving L-amino acid production, for example, for production of L-threonine, L-lysine, L-histidine, L-phenylalanine, L-arginine, L-tryptophan, and L-glutamic acid.

2. Background Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition by the resulting L-amino acid (see, for example, WO 95/16042 or U.S. Pat. Nos. 4,346,170, 5,661,012 and 6,040,160).

Strains useful in production of L-threonine by fermentation are known, including strains with increased activities of enzymes involved in L-threonine biosynthesis (U.S. Pat. Nos. 5,175,107; 5,661,012; 5,705,371; 5,939,307; EP 0219027), strains resistant to chemicals such as L-threonine and its analogs (WO 01/14525A1, EP 301572 A2, U.S. Pat. No. 5,376,538), strains with target enzymes desensitized to feedback inhibition by the produced L-amino acid or its by-products (U.S. Pat. Nos. 5,175,107; 5,661,012), and strains with inactivated threonine degradation enzymes (U.S. Pat. Nos. 5,939,307; 6,297,031).

The known threonine-producing strain VKPM B-3996 (U.S. Pat. Nos. 5,175,107 and 5,705,371) is presently one of the best known threonine producers. To construct the VKPM B-3996 strain, several mutations and a plasmid, described below, were introduced into the parent strain *E. coli* K-12 (VKPM B-7). A mutant thrA gene (mutation thrA442) encodes aspartokinase homoserine dehydrogenase I and is resistant to feedback inhibition by threonine. A mutant ilvA gene (mutation ilvA442) encodes threonine deaminase which has a decreased activity, and results in a decreased rate of isoleucine biosynthesis and a leaky phenotype of isoleucine starvation. In bacteria containing the ilvA442 mutation, transcription of the thrABC operon is not repressed by isoleucine, and therefore, these strains are very efficient for threonine production. Inactivation of the tdh gene results in prevention of threonine degradation. The genetic determinant of saccharose assimilation (scrKYABR genes) was transferred to said strain. To increase expression of the genes controlling threonine biosynthesis, the plasmid pVIC40 containing the mutant threonine operon thrA442BC was introduced into the intermediate strain TDH6. The amount of L-threonine which accumulates during fermentation of the strain can be up to 85 g/l.

By optimizing the main biosynthetic pathway of a desired compound, further improvement of L-amino acid producing strains can be accomplished via supplementation of the bacterium with increasing amounts of sugars as a carbon source, for example, glucose. Despite the efficiency of glucose transport by PTS, access to the carbon source in a highly productive strain still may be insufficient.

It is known that the active transport of sugars and other metabolites into bacterial cells is accomplished by several transport systems.

Among these, there are two inducible transport systems for L-arabinose utilization. The low-affinity permease ($K_M$ about 0.1 mM) is encoded by the araE gene at min 61.3 and the high-affinity system ($K_M$; 1 to 3 µM) is specified by the araFG operon at min 44.8. The araF gene encodes a periplasmic binding protein (306 amino acids) with chemotactic receptor function and the araG locus encodes at least one inner membrane protein. Both high- and low-affinity transports are under the control of the araC gene product and are thus part of the ara regulon (*Escherichia coli* and *Salmonella*, Second Edition, Editor in Chief: F. C. Neidhardt, ASM Press, Washington D.C., 1996). Studies in membrane vesicles have shown that L-arabinose permease can transport L-arabinose with low affinity (140-320 µM) and that arabinose transport is coupled with proton transport (Daruwalla, K. R. et al, Biochem. J., 200(3); 611-27 (1981)). L-arabinose permease is a member of the major facilitator superfamily (MFS) of transporters (Griffith, J. K. et al, Curr. Opin. Cell Biol. 4(4); 684-95 (1992)). Imported arabinose is catabolized to xylulose-5-phosphate by a set of enzymes encoded by the araBAD operon, and thence via the pentose phosphate pathway (*Escherichia coli* and *Salmonella*, Second Edition, Editor in Chief: F. C. Neidhardt, ASM Press, Washington D.C., 1996).

However, there have been no reports to date of using a bacterium of the Enterobacteriaceae family having an enhanced activity of L-arabinose permease for increasing the production of L-amino acids.

SUMMARY OF THE INVENTION

Objects of the present invention include enhancing the productivity of L-amino acid-producing strains and providing a method for producing non-aromatic or aromatic L-amino acids using these strains.

The above objects were achieved by finding that increasing the expression of the araE gene encoding L-arabinose permease can enhance production of L-amino acids, such as L-threonine, L-lysine, L-histidine, L-phenylalanine, L-arginine, L-tryptophan, and L-glutamic acid.

It is an object of the present invention to provide an L-amino acid-producing bacterium of the Enterobacteriaceae family, wherein said bacterium has been modified to enhance an activity of L-arabinose permease.

It is a further object of the present invention to provide the bacterium described above, wherein the activity of L-arabinose permease is enhanced by increasing the expression of a gene which encodes L-arabinose permease.

It is a further object of the present invention to provide the bacterium described above, wherein the activity of L-arabinose permease is enhanced by modifying an expression control sequence of the gene encoding L-arabinose permease so that the gene expression is enhanced or by increasing the copy number of the gene encoding L-arabinose permease.

It is a further object of the present invention to provide the bacterium described above, wherein said bacterium has been additionally modified to enhance an activity of glucokinase.

It is a further object of the present invention to provide the bacterium described above, where said bacterium has been additionally modified to enhance an activity of xylose isomerase.

It is a further object of the present invention to provide the bacterium described above, wherein said bacterium is selected from the group consisting of the genera *Escherichia, Enterobacter, Erwinia, Klebsiella, Pantoea, Providencia, Salmonella, Serratia, Shigella,* and *Morganella*.

It is a further object of the present invention to provide the bacterium described above, wherein said gene encodes an L-arabinose permease selected from the group consisting of:
  (A) a protein which comprises the amino acid sequence of SEQ ID NO: 2; and
  (B) a variant protein of the amino acid sequence shown in SEQ ID NO: 2, and which has an activity of L-arabinose permease.

It is a further object of the present invention to provide the bacterium described above, wherein said gene encoding L-arabinose permease comprises a DNA selected from the group consisting of:
  (a) a DNA which comprises a nucleotide sequence of nucleotides 1 to 1419 in SEQ ID NO: 1; and
  (b) a DNA which is hybridizable with a nucleotide sequence of nucleotides 1-1419 in SEQ ID NO: 1, or a probe which can be prepared from said nucleotide sequence under stringent conditions, and encodes a protein having an activity of L-arabinose permease.

It is a further object of the present invention to provide the bacterium described above, wherein said stringent conditions comprise those in which washing is performed at 60° C. at a salt concentration of 1×SSC and 0.1% SDS, for approximately 15 minutes.

It is a further object of the present invention to provide the bacterium described above, wherein said bacterium is an L-threonine producing bacterium.

It is a further object of the present invention to provide the bacterium described above, wherein said bacterium has been further modified to enhance expression of one or more of the genes selected from the group consisting of
  the mutant thrA gene which codes for aspartokinase homoserine dehydrogenase I and is resistant to feedback inhibition by threonine;
  the thrB gene which codes for homoserine kinase;
  the thrC gene which codes for threonine synthase;
  the rhtA gene which codes for a putative transmembrane protein;
  the asd gene which codes for aspartate-β-semialdehyde dehydrogenase; and
  the aspC gene which codes for aspartate aminotransferase (aspartate transaminase).

It is a further object of the present invention to provide the bacterium described above, wherein said bacterium has been modified to increase expression of said mutant thrA gene, said thrB gene, said thrC gene, and said rhtA gene.

It is a further object of the present invention to provide the bacterium described above, wherein said bacterium is an L-lysine producing bacterium.

It is a further object of the present invention to provide the bacterium described above, wherein said bacterium is an L-histidine producing bacterium.

It is a further object of the present invention to provide the bacterium described above, wherein said bacterium is an L-phenylalanine producing bacterium.

It is a further object of the present invention to provide the bacterium described above, wherein said bacterium is an L-arginine producing bacterium.

It is a further object of the present invention to provide the bacterium described above, wherein said bacterium is an L-tryptophan producing bacterium.

It is a further object of the present invention to provide the bacterium described above, wherein said bacterium is an L-glutamic acid producing bacterium.

It is a further object of the present invention to provide a method for producing an L-amino acid which comprises cultivating the bacterium described above in a culture medium, allowing accumulation of the L-amino acid in the culture medium, and isolating the L-amino acid from the culture medium.

It is a further object of the present invention to provide the method described above, wherein said L-amino acid is L-threonine.

It is a further object of the present invention to provide the method described above, wherein said L-amino acid is L-lysine.

It is a further object of the present invention to provide the method described above, wherein said L-amino acid is L-histidine.

It is a further object of the present invention to provide the method described above, wherein said L-amino acid is L-phenylalanine.

It is a further object of the present invention to provide the method described above, wherein said L-amino acid is L-arginine.

It is a further object of the present invention to provide the method described above, wherein said L-amino acid is L-tryptophan.

It is a further object of the present invention to provide the method described above, wherein said L-amino acid is L-glutamic acid.

BRIEF DESCRIPTION OF THE DRAWINGS

FIG. 2 shows the alignment of the primary sequences of arabinose permease from *Escherichia coli* (Ec), *Shigella flexneri* (Sj), *Salmonella typhimurium* (St), *Klebsiella oxytoca* (Ko) and *Bacillus subtilis* (Bs). The alignment was done by using the PIR Multiple Alignment program (//pir.georgetown.edu). The identical amino acids are marked by asterisk (*), similar amino acids are marked by colon (:).

DETAILED DESCRIPTION OF THE PREFERRED EMBODIMENTS

Figure 1:
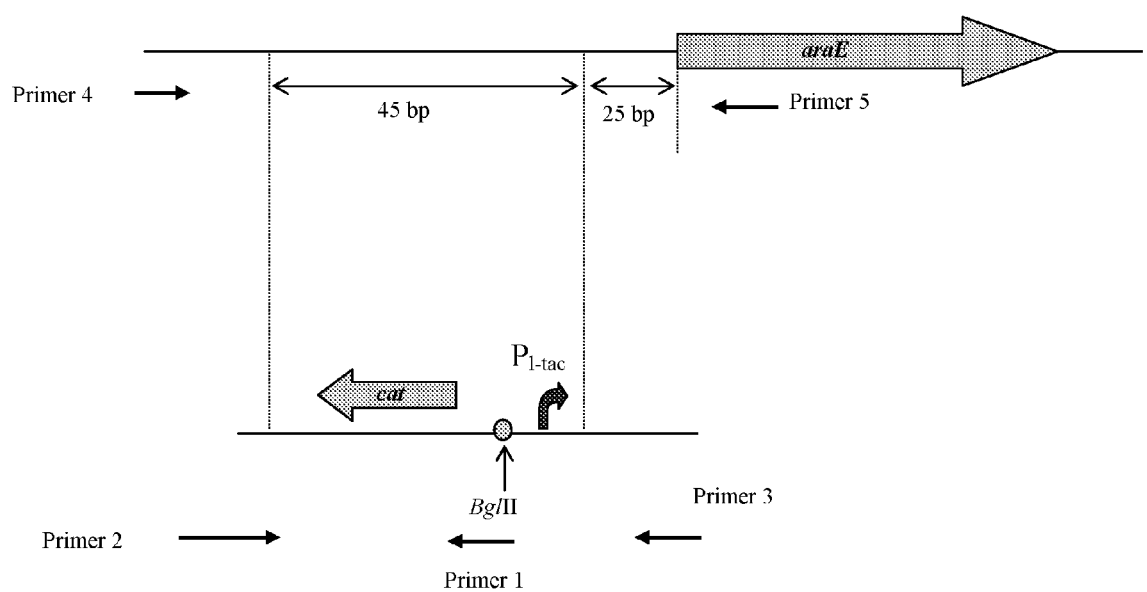
FIG. 1 shows the structure of the region upstream of the araE gene in the chromosome of *E. coli* and the structure of an integrated DNA fragment containing the cat gene and a hybrid $P_{L-tac}$ promoter.

In the present invention, "L-amino acid-producing bacterium" means a bacterium which has an ability to cause accumulation of an L-amino acid in a medium when the bacterium is cultured in the medium. The L-amino acid-producing ability may be imparted or enhanced by breeding. The phrase "L-amino acid-producing bacterium" as used herein also means a bacterium which is able to produce and cause accumulation of an L-amino acid in a culture medium in amount larger than a wild-type or parental strain of *E. coli*, such as *E. coli* K-12, and preferably means that the microorganism is able to cause accumulation in a medium of an amount not less than 0.5 g/L, more preferably not less than 1.0 g/L of the target L-amino acid. "L-amino acids" include L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. L-threonine, L-lysine, L-histidine, L-phenylalanine, L-arginine, L-tryptophan, and L-glutamic acid are particularly preferred.

The Enterobacteriaceae family includes bacteria belonging to the genera *Escherichia, Enterobacter, Erwinia, Klebsiella, Pantoea, Providencia, Salmonella, Serratia, Shigella, Morganella*, etc. Specifically, bacteria classified into the Enterobacteriaceae family according to the taxonomy used in the NCBI (National Center for Biotechnology Information) database (//www.ncbi.nlm.nih.gov/htbinpost/Taxonomy/wgetorg?mode=Tree&id=1236&lvl=3&keep=1&srchmode=1&unlock) can be used. A bacterium belonging to the genus *Escherichia* or *Pantoea* is preferred.

The phrase "a bacterium belonging to the genus *Escherichia*" means that the bacterium is classified in the genus *Escherichia* according to the classification known to a person skilled in the art of microbiology. Examples of a microorganism belonging to the genus *Escherichia* as used in the present invention include, but are not limited to, *Escherichia coli (E. coli)*.

The bacterium belonging to the genus *Escherichia* that can be used in the present invention is not particularly limited, however for example, bacteria described by Neidhardt, F. C. et al. (*Escherichia coli* and *Salmonella typhimurium*, American Society for Microbiology, Washington D.C., 1208, Table 1) are encompassed by the present invention.

The phrase "a bacterium belonging to the genus *Pantoea*" means that the bacterium is classified into the genus *Pantoea* according to the classification known to a person skilled in the art of microbiology. Some species of *Enterobacter agglomerans* have been recently re-classified into *Pantoea agglomerans, Pantoea ananatis, Pantoea stewartii*, or the like, based on the nucleotide sequence analysis of 16S rRNA etc. (Int. J. Syst. Bacteriol., 43, 162-173 (1993)).

The bacterium of the present invention encompasses a strain of the Enterobacteriaceae family which has an ability to produce an L-amino acid and has been modified to enhance an activity of L-arabinose permease. In addition, the bacterium of the present invention encompasses a strain of the Enterobacteriaceae family which has an ability to produce an L-amino acid and does not have a native activity of L-arabinose permease, and has been transformed with a DNA fragment encoding L-arabinose permease.

The phrase "activity of L-arabinose permease" means an activity of transporting sugars, such as L-arabinose and glucose, into the cell. Activity of L-arabinose permease can be detected and measured by the method described by Henderson P. J. and Macpherson A. J. (Methods Enzymol., 125, 387-429 (1986)).

The phrase "modified to enhance an activity of L-arabinose permease" means that the activity per cell is higher as compared to that of a non-modified strain, for example, a wild-type strain. Examples of such modifications include increasing the number of L-arabinose permease molecules per cell, increasing the specific activity per L-arabinose permease molecule, and so forth. Furthermore, a wild-type strain that may be used for comparison purposes includes, for example, *Escherichia coli* K-12. In the present invention, the amount of accumulated L-amino acid, for example, L-threonine, L-lysine, L-histidine, L-phenylalanine, L-arginine, L-tryptophan, or L-glutamic acid, can be increased in a culture medium as a result of enhancing the intracellular activity of L-arabinose permease.

Enhancing L-arabinose permease activity in a bacterial cell can be attained by increasing the expression of the araE gene encoding L-arabinose permease. Any araE gene derived from bacteria belonging to the genus *Escherichia*, as well as any araE gene derived from other bacteria, such as bacteria belonging to the genus *Bacillus, Klebsiella, Pantoea, Salmonella*, or *Shigella*, may be used as the L-arabinose permease gene of the present invention. araE genes derived from bacteria belonging to the genus *Escherichia* are preferred.

The phrase "increasing the expression of the gene" means that the expression of the gene is higher than that of a non-modified strain, for example, a wild-type strain. Examples of such modification include increasing the copy number of expressed gene(s) per cell, increasing the expression level of the gene(s), and so forth. The quantity of the copy number of an expressed gene is measured, for example, by restricting the chromosomal DNA followed by Southern blotting using a probe based on the gene sequence, fluorescence in situ hybridization (FISH), and the like. The level of gene expression can be measured by various known methods including Northern blotting, quantitative RT-PCR, and the like. Furthermore, wild-type strains that can act as a control include, for example, *Escherichia coli* K-12 or *Pantoea ananatis* FERM BP-6614. As a result of enhancing the intracellular activity of L-arabinose permease, L-amino acid accumulation, for example L-threonine, L-lysine, L-histidine, L-phenylalanine, L-tryptophan, or L-glutamic acid accumulation in a medium is observed.

The araE gene which encodes L-arabinose permease, namely the L-arabinose/proton symporter, from *Escherichia coli* has been elucidated (nucleotide numbers complement to numbers 2978786 to 2980204 in the sequence of GenBank accession NC_000913.2, gi:49175990). The araE gene is located between ydeA ORF and kduD gene on the chromosome of *E. coli* K-12. Other araE genes which encode L-arabinose permease have also been elucidated: araE gene from *Shigella flexneri* (nucleotide numbers complement to numbers 2935806 to 2937224 in the sequence of GenBank accession NP_838353.1, gi:30064182); araE gene from *Salmonella typhimurium* LT2 (nucleotide numbers complement to numbers 3175802 to 3177220 in the sequence of GenBank accession NP_461933.1; gi: 16766318), araE gene from *Klebsiella oxytoca* (locus P45598; gi: 1168483), and the like. In the present invention, the araE gene from *Escherichia coli* is represented by SEQ ID NO. 1.

Upon being transported into the cell, glucose is phosphorylated by glucokinase, which is encoded by the glk gene. So, it is also desirable to modify the bacterium to have enhanced activity of glucokinase. The glk gene which encodes glucokinase of *Escherichia coli* has been elucidated (nucleotide numbers 2506-481 to 2507-446 in the sequence of GenBank accession NC_000913.1, gi: 16127994). The glk gene is located between the b2387 and the b2389 ORFs on the chromosome of *E. coli* K-12.

Under appropriate conditions, the xylose isomerase encoded by the xylA gene also efficiently catalyzes the conversion of D-glucose to D-fructose (Wovcha, M. G. et al, Appl Environ Microbiol. 45(4): 1402-4 (1983)). So, it is also desirable to modify the bacterium to have an enhanced activity of xylose isomerase. The xylA gene which encodes xylose isomerase of *Escherichia coli* has been elucidated (nucleotide numbers 3728788 to 3727466 in the sequence of GenBank accession NC_000913.2, gi: 49175990). The xylA gene is located between xylB and xylF genes on the chromosome of *E. coli* K-12.

Therefore, araE, glk and xylA genes can be obtained by PCR (polymerase chain reaction; refer to White, T. J. et al., Trends Genet., 5, 185 (1989)) utilizing primers prepared based on the known nucleotide sequence of the gene. Genes coding for L-arabinose permease from other microorganisms can be obtained in a similar manner.

The araE gene derived from *Escherichia coli* is exemplified by a DNA which encodes the following protein (A) or (B):

(A) a protein which has the amino acid sequence shown in SEQ ID NO: 2; or (B) a variant protein of the amino acid sequence shown in SEQ ID NO: 2, which has an activity of L-arabinose permease.

The phrase "variant protein" as used in the present invention means a protein which has changes in the sequence, whether they are deletions, insertions, additions, or substitutions of amino acids, but still maintains the desired activity at a useful level, for example, useful for the enhanced production of an L-amino acid. The number of changes in the variant protein depends on the position or the type of amino acid residue in the three dimensional structure of the protein. The number of changes may be 1 to 30, preferably 1 to 15, and more preferably 1 to 5 for the protein (A). These changes in the variants can occur in regions of the protein which are not critical for the function of the protein. This is because some amino acids have high homology to one another so the three dimensional structure or activity is not affected by such a change. These changes in the variant protein can occur in regions of the protein which are not critical for the function of the protein. Therefore, the protein variant (B) may be one which has a homology of not less than 70%, preferably 80%, and more preferably 90%, and most preferably 95% with respect to the entire amino acid sequence of L-arabinose permease shown in SEQ ID NO. 2, as long as the activity of L-arabinose permease is maintained. Homology between two amino acid sequences can be determined using the well-known methods, for example, the computer program BLAST 2.0, which calculates three parameters: score, identity and similarity.

The substitution, deletion, insertion, or addition of one or several amino acid residues should be conservative mutation(s) so that the activity is maintained. The representative conservative mutation is a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

Earlier it was shown that sugar transporters of MFS, such as D-xylose/H+ symporter (XylE), L-arabinose/H+ symporter (AraE) and D-galactose/H+ symporter (GalP), have high homology, having at least 28% identical amino acid residues conserved in the aligned sequences of these proteins (Henderson, P. J. and Maiden M. C., Philos Trans R Soc Lond B Biol Sci., 30, 326(1236), 391-410 (1990)). A comparison of the primary sequences of arabinose permease from *Escherichia coli, Shigella flexneri, Salmonella typhimurium, Klebsiella oxytoca*, and *Bacillus subtilis* also show a high level of homology among these proteins (see FIG. 2). From this point of view, substitutions or deletions of the amino acid residues which are identical in all the above-mentioned proteins could be crucial for their function, whereas modifications of other non-conserved amino acid residues may not lead to alteration of the activity of L-arabinose permease.

The DNA, which encodes substantially the same protein as the L-arabinose permease described above, may be obtained, for example, by modifying the nucleotide sequence of DNA encoding L-arabinose permease (SEQ ID NO: 1), for example, by means of the site-directed mutagenesis method so that one or more amino acid residues at a specified site involve deletion, substitution, insertion, or addition. DNA modified as described above may be obtained by conventionally known mutation treatments. Such treatments include hydroxylamine treatment of the DNA encoding proteins of present invention, or treatment of the bacterium containing the DNA with UV irradiation or a reagent such as N-methyl-N'-nitro-N-nitrosoguanidine or nitrous acid.

A DNA encoding substantially the same protein as L-arabinose permease can be obtained by expressing DNA having a mutation as described above in an appropriate cell, and investigating the activity of any expressed product. A DNA encoding substantially the same protein as L-arabinose permease can also be obtained by isolating a DNA that is hybridizable with a probe having a nucleotide sequence which contains, for example, the nucleotide sequence shown as SEQ ID NO: 1, under the stringent conditions, and encodes a protein having the L-arabinose permease activity. The "stringent conditions" referred to herein are conditions under which so-called specific hybrids are formed, and non-specific hybrids are not formed. For example, stringent conditions can be exemplified by conditions under which DNAs having high homology, for example, DNAs having homology of not less than 50% are able to hybridize with each other, but DNAs having homology lower than 50% are not able to hybridize with each other. Alternatively, stringent conditions may be exemplified by conditions under which DNA is able to hybridize at a salt concentration equivalent to ordinary washing conditions in Southern hybridization, i.e., 1×SSC, 0.1% SDS, preferably 0.1×SSC, 0.1% SDS, at 60° C. Duration of washing depends on the type of membrane used for blotting and, as a rule, what is recommended by the manufacturer. For example, recommended duration of washing the Hybond™ N+ nylon membrane (Amersham) under stringent conditions is 15 minutes.

A partial sequence of the nucleotide sequence of SEQ ID NO: 1 can also be used as a probe. Probes may be prepared by PCR using primers based on the nucleotide sequence of SEQ ID NO: 1, and a DNA fragment containing the nucleotide sequence of SEQ ID NO: 1 as a template. When a DNA fragment having a length of about 300 bp is used as the probe, the hybridization conditions for washing include, for example, 50° C., 2×SSC and 0.1% SDS.

The substitution, deletion, insertion, or addition of nucleotides as described above also includes a mutation which naturally occurs (mutant or variant), for example, due to variety in the species or genus of bacterium, and which contains the L-arabinose permease.

"Transformation of a bacterium with DNA encoding a protein" means introduction of the DNA into a bacterium, for example, by conventional methods. Transformation of this DNA will result in an increase in expression of the gene encoding the protein of present invention, and will enhance the activity of the protein in the bacterial cell. Methods of transformation include any known methods that have hitherto been reported. For example, a method of treating recipient cells with calcium chloride so as to increase permeability of the cells to DNA has been reported for *Escherichia coli* K-12 (Mandel, M. and Higa, A., *J. Mol. Biol.*, 53, 159 (1970)) and may be used.

Methods of gene expression enhancement include increasing the gene copy number. Introducing a gene into a vector that is able to function in a bacterium of the Enterobacteriaceae family increases the copy number of the gene. Preferably, low copy vectors are used. Examples of low-copy vectors include but are not limited to pSC101, pMW118, pMW119, and the like. The term "low copy vector" is used for vectors, the copy number of which is up to 5 copies per cell.

Enhancement of gene expression may also be achieved by introduction of multiple copies of the gene into a bacterial chromosome by, for example, a method of homologous recombination, Mu integration, or the like. For example, one act of Mu integration allows introduction of up to 3 copies of the gene into a bacterial chromosome.

Increasing the copy number of the L-arabinose permease gene can also be achieved by introducing multiple copies of the L-arabinose permease gene into the chromosomal DNA of the bacterium. In order to introduce multiple copies of the gene into a bacterial chromosome, homologous recombination is carried out using a sequence whose multiple copies exist as targets in the chromosomal DNA. Sequences having multiple copies in the chromosomal DNA include, but are not limited to repetitive DNA, or inverted repeats existing at the end of a transposable element. Also, as disclosed in U.S. Pat. No. 5,595,889, it is possible to incorporate the L-arabinose permease gene into a transposon, and allow it to be transferred to introduce multiple copies of the gene into the chromosomal DNA.

Enhancing gene expression may also be achieved by placing the DNA of the present invention under the control of a potent promoter. For example, the lac promoter, the trp promoter, the trc promoter, the $P_R$, or the $P_L$ promoters of lambda phage are all known to be potent promoters. The use of a potent promoter can be combined with multiplication of gene copies.

Alternatively, the effect of a promoter can be enhanced by, for example, introducing a mutation into the promoter to increase the transcription level of a gene located downstream of the promoter. Furthermore, it is known that substitution of several nucleotides in the spacer between ribosome binding site (RBS) and the start codon, especially the sequences immediately upstream of the start codon, profoundly affect the mRNA translatability. For example, a 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984). Previously, it was shown that the rhtA23 mutation is an A-for-G substitution at the −1 position relative to the ATG start codon (ABSTRACTS of $17^{th}$ International Congress of Biochemistry and Molecular Biology in conjugation with 1997 Annual Meeting of the American Society for Biochemistry and Molecular Biology, San Francisco, Calif. Aug. 24-29, 1997, abstract No. 457). Therefore, it may be suggested that the rhtA23 mutation enhances the rhtA gene expression and, as a consequence, increases the resistance to threonine, homoserine and some other substances transported out of cells.

Moreover, it is also possible to introduce a nucleotide substitution into a promoter region of the L-arabinose permease gene on the bacterial chromosome, which results in a stronger promoter function. The alteration of the expression control sequence can be performed, for example, in the same manner as the gene substitution using a temperature-sensitive plasmid, as disclosed in WO 00/18935 and JP 1-215280 A.

Methods for preparation of plasmid DNA include, but are not limited to digestion and ligation of DNA, transformation, selection of an oligonucleotide as a primer and the like, or other methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

The bacterium of the present invention can be obtained by introduction of the aforementioned DNAs into a bacterium which inherently has the ability to produce L-amino acid. Alternatively, the bacterium of the present invention can be obtained by imparting an ability to produce L-amino acid to the bacterium already containing the DNAs.

L-threonine Producing Bacteria

Examples of parent strains for deriving the L-threonine producing bacteria of the present invention include, but are not limited to, strains belonging to the genus *Escherichia*, such as *E. coli* TDH-6/pVIC40 (VKPM B-3996) (U.S. Pat. Nos. 5,175,107, 5,705,371), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting into RSF1010-derived vector a thrA*BC operon which includes a mutant thrA gene. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Nagatinskaya Street 3-A, 113105 Moscow, Russian Federation) under the accession number RIA 1867. The strain was also deposited in the Russian National Collection of Industrial Microorganisms (VKPM) (Dorozhny proezd 1, Moscow 117545, Russian Federation) on Apr. 7, 1987 under the accession number B-3996.

Preferably, the bacterium of the present invention is additionally modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase;

the aspC gene which codes for aspartate aminotransferase (aspartate transaminase);

The thrA gene which encodes aspartokinase homoserine dehydrogenase I of *Escherichia coli* has been elucidated (nucleotide numbers 337 to 2799 in the sequence of GenBank accession NC_000913.2, gi: 49175990). The thrA gene is located between thrL and thrB genes on the chromosome of *E. coli* K-12. The thrB gene which encodes homoserine kinase of *Escherichia coli* has been elucidated (nucleotide numbers 2801 to 3733 in the sequence of GenBank accession NC_000913.2, gi: 49175990). The thrB gene is located between thrA and thrC genes on the chromosome of *E. coli* K-12. The thrC gene which encodes threonine synthase of

*Escherichia coli* has been elucidated (nucleotide numbers 3734 to 5020 in the sequence of GenBank accession NC_000913.2, gi: 49175990). The thrC gene is located between thrB gene and yaaX opened reading frame on the chromosome of *E. coli* K-12. All three genes are functioning as one threonine operon.

A mutant thrA gene which codes for aspartokinase homoserine dehydrogenase I resistant to feed back inhibition by threonine, as well as, the thrB and thrC genes can be obtained as one operon from well-known plasmid pVIC40 which is presented in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, positions 764 to 1651, GenBank accession no. AAA218541, gi:440181) and located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position-1 with respect to the ATG start codon (ABSTRACTS of the 17$^{th}$ International Congress of Biochemistry and Molecular Biology in conjugation with the Annual Meeting of the American Society for Biochemistry and Molecular Biology, San Francisco, Calif., Aug. 24-29, 1997, abstract No. 457, EP 1013765 A).

The asd gene of *E. coli* has already been elucidated (nucleotide positions 3572511 to 3571408, GenBank accession no. NC_000913.1, gi:16131307), and can be obtained by PCR (polymerase chain reaction; refer to White, T. J. et al., Trends Genet., 1989, 5:185), utilizing primers based on the nucleotide sequence of the gene. The asd genes of other microorganisms can be obtained in a similar manner.

Also, the aspC gene of *E. coli* has already been elucidated (nucleotide positions 983742 to 984932, GenBank accession no. NC_000913.1, gi: 16128895), and can be obtained by PCR. The aspC genes of other microorganisms can be obtained in a similar manner.

L-lysine Producing Bacteria

Examples of L-lysine producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine coexists in a medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346, 170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069, and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (see U.S. Pat. No. 5,827,698).

Examples of parent strains for deriving L-lysine-producing bacteria of the present invention also include strains in which expression of one or more genes encoding an L-lysine biosynthetic enzyme are enhanced. Examples of the enzymes involved in L-lysine biosynthesis include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), nicotinamide adenine dinucleotide transhydrogenase (pntAB), and aspartase (aspA) (EP 1253195 A).

Examples of parent strains for deriving L-lysine-producing bacteria of the present invention also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase and lysine decarboxylase (U.S. Pat. No. 5,827,698).

L-histidine Producing Bacteria

Examples of parent strains for deriving L-histidine producing bacteria of the present invention include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* A180/pFM201 (U.S. Pat. No. 6,258,554), and the like.

Examples of parent strains for deriving L-histidine-producing bacteria of the present invention also include strains in which expression of one or more genes encoding an L-histidine biosynthetic enzyme are enhanced. Examples of the L-histidine-biosynthetic enzymes include ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (his H), histidinol phosphate aminotransferase (his C), histidinol phosphatase (hisB), histidinol dehydrogenase (hisD), and so forth.

It is known that the genes encoding the L-histidine biosynthetic enzyme (hisG, hisBHAFI) are inhibited by L-histidine, and therefore an L-histidine-producing ability can also be efficiently enhanced by introducing a mutation conferring resistance to the feedback inhibition into ATP phosphoribosyltransferase (hisG) (Russian Patent Nos. 2003677 and 2119536).

Specific examples of strains having an L-histidine-producing ability include *E. coli* FERM-P 5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-phenylalanine Producing Bacteria

Examples of parent strains for deriving L-phenylalanine producing strains of the present invention include, but are not limited to, strains belonging to the genus *Escherichia*, such as *E. coli* AJ12739 (tyrA::Tn10, tyrR) (VKPM B-8197); *E. coli* HW1089 (ATCC Accession No. 55371) harboring pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952), and the like. Also, as a parent strain which can be enhanced in activity of the protein of the present invention, L-phenylalanine-producing bacteria belonging to the genus *Escherichia*, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named A J 12604 (FERM BP-3579) may be used (EP 488424 B1). Furthermore, L-phenylalanine producing bacteria belonging to the genus *Escherichia* with an enhanced activity of a protein encoded by the yedA gene or the yddG gene may also be used (U.S. Patent Applications 2003/0148473 A1 and 2003/0157667 A1).

L-arginine Producing Bacteria

Examples of parent strains for deriving L-arginine producing bacteria of the present invention include, but are not limited to, strains belonging to the genus *Escherichia*, such as *E. coli* mutants having resistance to α-methylmethionine, p-fluorophenylalanine, D-arginine, arginine hydroxamate, S-(2-aminoethyl)-cysteine, α-methylserine, β-2-thienylalanine, or sulfaguanidine (JP 56-106598A); an L-arginine-producing strain into which the argA gene encoding N-acetylglutamate synthetase is introduced (EP1170361A1); *E. coli* strains 237 (VKPM B-7925) and 382 (VKPM B-7926) described in EP1170358A1, and the like.

Examples of parent strains for deriving L-arginine producing bacteria of the present invention also include strains in which expression of one or more genes encoding an L-arginine biosynthetic enzyme are enhanced. Examples of the L-arginine biosynthetic enzymes include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase. These arginine biosynthetic genes exist on the Arg operon (argCJBDFRGH), and are regulated by an arginine repressor encoded by argR (J Bacteriol. 2002 December; 184(23):6602-14). Therefore, disruption of the arginine repressor results in an increase in the expression of the Arg operon, thus enhancing the activities of the L-arginine-producing enzymes (U.S. Patent Application 2002/0045223 A1).

L-tryptophan Producing Bacteria

Examples of parent strains for deriving the L-tryptophan-producing bacteria of the present invention include, but are not limited to, strains belonging to the genus *Escherichia*, such as *E. coli* JP4735/pMU3028 (DSM10122) and JP6015/pMU91 (DSM10123) deficient in the tryptophanyl-tRNA synthetase encoded by a mutant trpS gene (U.S. Pat. No. 5,756,345); *E. coli* SV164 (pGH5) having the serA allele free from feedback inhibition by serine (U.S. Pat. No. 6,180,373); *E. coli* AGX17 (pGX44) (NRRL B-12263) and AGX6 (pGX50)aroP (NRRL B-12264) deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like, may be used.

Previously, it was identified that the yddG gene encodes a membrane protein which is not involved in a biosynthetic pathway of any L-amino acid, and imparts to a microorganism resistance to L-phenylalanine and several amino acid analogues when the wild-type allele of the gene was amplified on a multi-copy vector in the microorganism. Besides, the yddG gene can enhance production of L-phenylalanine or L-tryptophan when additional copies are introduced into the cells of the respective producing strain (WO03044192). So, it is desirable that the L-tryptophan-producing bacterium be further modified to have enhanced expression of the yddG open reading frame.

Examples of parent strains for deriving the L-tryptophan-producing bacteria of the present invention also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include a *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains for deriving the L-tryptophan-producing bacteria of the present invention also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by trpA and trpB, respectively.

L-glutamic Acid Producing Bacteria

Examples of parent strains for deriving the L-glutamic acid-producing bacteria of the present invention include, but are not limited to, strains in which expression of one or more genes encoding an L-glutamic acid biosynthetic enzyme are enhanced. Examples of the enzymes involved in L-glutamic acid biosynthesis include glutamate dehydrogenase, glutamine synthetase, glutamate synthetase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phophate dehydrogenase, triose phosphate isomerase, fructose bisphosphate aldolase, phosphofructokinase, and glucose phosphate isomerase.

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains for deriving the L-glutamic acid-producing bacteria of the present invention also include strains having decreased or eliminated activity of an enzyme that catalyzes synthesis of a compound other than L-glutamic acid, and branching off from an L-glutamic acid biosynthesis pathway. Examples of such enzymes include isocitrate lyase, α-ketoglutarate dehydrogenase, phosphotransacetylase, acetate kinase, acetohydroxy acid synthase, acetolactate synthase, formate acetyltransferase, lactate dehydrogenase, and glutamate decarboxylase.

Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::Kmr is a strain which is obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in the α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671); AJ131318 (FERM BP-5565) (U.S. Pat. No. 6,110,714), and the like.

Examples of L-glutamic acid-producing bacteria include mutant strains belonging to the genus *Pantoea* which are deficient in the α-ketoglutarate dehydrogenase activity or have a decreased α-ketoglutarate dehydrogenase activity, and can be obtained as described above. Such strains include *Pantoea ananatis* AJ13356 (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 and received an accession number of FERM P-16645. It was then converted to an international deposit under the provisions of the Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

Production of L-Amino Acids

Oxaloacetate (OAA) serves as a substrate for the reaction which results in synthesis of Thr and Lys. OAA results from a reaction of PEP with phosphoenol pyrvate carboxlase (PEPC) functioning as a catalyst. Therefore, elevation of the PEPC concentration in a cell can be very important for fermentative production of these amino acids. When using glucose as the carbon source in fermentation, glucose is internalized by the glucose-phosphontransferase (Glc-PTS) system. This system consumes PEP, and proteins in the PTS are encoded by ptsG and ptsHIcrr. During internalization, one molecule of PEP and one molecule of pyruvate (Pyr) are generated from one molecule of glucose.

An L-threonine-producing strain and an L-lysine-producing strain which have been modified to have an ability to utilize sucrose (Scr-PTS) have higher productivity of these amino acids when cultured in sucrose rather than glucose (EP 1149911 A2). It is believed that three molecules of PEP and one molecule of Pyr are generated from one molecule of sucrose by the Scr-PTS, increasing the ratio of PEP/Pyr, and thereby facilitating the synthesis of Thr and Lys from sucrose. Furthermore, it has been reported that Glc-PTS is subject to several expression controls (Postma P. W. et al., Microbiol Rev., 57(3), 543-94 (1993); Clark B. et al. J. Gen. Microbiol., 96(2), 191-201 (1976); Plumbridge J., Curr. Opin. Microbiol., 5(2), 187-93 (2002); Ryu S. et al., J. Biol. Chem., 270(6):2489-96 (1995)), and hence it is possible that the incorporation of glucose itself can be a rate-limiting step in amino acid fermentation.

Increasing the ratio of PEP/Pyr even more by increasing expression of the araE gene in a threonine-producing strain, a lysine-producing strain, an histidine-producing strain, a phenylalanine-producing strain, an arginine-producing strain, a tryptophan-producing strain and/or a glutamic acid—producing strain should further increase amino acid production. Because four molecules of PEP are generated from two molecules of glucose, the ratio of PEP/Pyr is expected to be greatly improved. Due to the increased expression of the araE gene, removal of the expression control glc-PTS is expected.

The method for producing an L-amino acid of the present invention includes the steps of cultivating the bacterium of the present invention in a culture medium, allowing L-amino acid to accumulate in the culture medium, and collecting L-amino acid from the culture medium. Furthermore, the method of present invention includes a method for producing L-threonine, L-lysine, L-histidine, L-phenylalanine, L-arginine, L-tryptophan, or L-glutamic acid, including the steps of cultivating the bacterium of the present invention in a culture medium, allowing L-threonine, L-lysine, L-histidine, L-phenylalanine, L-arginine, L-tryptophan, or L-glutamic acid to accumulate in the culture medium, and collecting L-threonine, L-lysine, L-histidine, L-phenylalanine, L-arginine, L-tryptophan, or L-glutamic acid from the culture medium.

In the present invention, the cultivation, collection, and purification of L-amino acids from the medium and the like may be performed by conventional fermentation methods wherein an L-amino acid is produced using a microorganism.

The culture medium may be either synthetic or natural, so long as the medium includes a carbon source and a nitrogen source and minerals, and if necessary, appropriate amounts of nutrients which the microorganism requires for growth. The carbon source may include various carbohydrates such as glucose and sucrose, and various organic acids. Depending on the mode of assimilation of the chosen microorganism, alcohols, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganisms may be used. As minerals, potassium monophosphate, magnesium sulfate, sodium chloride, ferrous sulfate, manganese sulfate, calcium chloride, and the like may be used. As vitamins, thiamine, yeast extract, and the like may be used. Additional nutrients may be added to the medium, if necessary. For example, if the microorganism requires an L-amino acid for growth (L-amino acid auxotrophy), a sufficient amount of the L-amino acid may be added to the cultivation medium.

The cultivation is performed preferably under aerobic conditions such as a shaking culture, and stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then target L-amino acids can be collected and purified by ion-exchange, concentration, and crystallization methods.

EXAMPLES

The present invention will be more concretely explained below with reference to the following non-limiting examples.

Example 1

Substitution of the Native Promoter Region of araE Gene in *E. coli* by Hybrid $P_{L\text{-}tac}$ Promoter To substitute the native promoter region of the araE gene, a DNA fragment carrying a hybrid $P_{L\text{-}tac}$ promoter and chloramphenicol resistance marker ($Cm^R$) encoded by the cat gene can be integrated into the chromosome of *E. coli* MG1655 (ATCC 700926) in place of the native promoter region by the method described by Datsenko K. A. and Wanner B. L. (Proc. Natl. Acad. Sci. USA, 2000, 97, 6640-6645), which is also called as a "Red-mediated integration" and/or "Red-driven integration". The recombinant plasmid pKD46 (Datsenko, K. A., Wanner, B. L., Proc. Natl. Acad. Sci. USA, 2000, 97, 6640-6645) having a thermosensitive replicon can be the donor of the phage λ-derived genes responsible for the Red-mediated recombination system. *Escherichia coli* BW25113 containing the recombinant plasmid pKD46 can be obtained from the *E. coli* Genetic Stock Center, Yale University, New Haven, USA, the accession number of which is CGSC7630.

The hybrid $P_{L\text{-}tac}$ promoter can be synthesized chemically. The nucleotide sequence of the substituted promoter is presented in the Sequence listing (SEQ ID NO: 3). The synthesized DNA fragment containing the hybrid $P_{L\text{-}tac}$ promoter contains a Bg/II recognition site at the 5'-end thereof, which is necessary for further joining to the cat gene, and 36 nucleotides homologous to the 5'-terminus of araE gene are introduced for further integration into the bacterial chromosome.

A DNA fragment containing a $Cm^R$ marker encoded by the cat gene can be obtained by PCR using the commercially available plasmid pACYC184 (GenBank/EMBL accession number X06403, "Fermentas", Lithuania) as the template, and primers P1 (SEQ ID NO: 4) and P2 (SEQ ID NO: 5). Primer P1 contains a Bg/II recognition site at the 5'-end thereof, which is necessary for further joining to the hybrid $P_{L\text{-}tac}$ promoter, and primer P2 contains 36 nucleotides homologous to the region located 70 bp upstream of the start codon of the araE gene, which is introduced into the primer for further integration into the bacterial chromosome.

PCR can be provided using the "TermoHybaid PCR Express" amplificator. The reaction mixture (total volume—50 µl) consists of 5 µl of 10× PCR-buffer with 15 mM $MgCl_2$ ("Fermentas", Lithuania), 200 µM each of dNTP, 25 pmol each of the exploited primers and 1 U of Taq-polymerase ("Fermentas", Lithuania). Approximately 5 ng of the plasmid DNA can be added to the reaction mixture as a template DNA for the PCR amplification. The following temperature profile can be used: initial DNA denaturation at 95° C. for 5 min, followed by 25 cycles of denaturation at 95° C. for 30 sec, annealing at 55° C. for 30 sec, elongation at 72° C. for 30 sec; and the final elongation at 72° C. for 7 min. Then, the amplified DNA fragments can be purified by agarose gel-electrophoresis, extracted using "GenElute Spin Columns" (Sigma, USA) and precipitated by ethanol.

Each of the two above-described DNA fragments can be treated with Bg/II restrictase and ligated. The ligation product can be amplified by PCR using primers P2 (SEQ ID NO: 5) and P3 (SEQ ID NO: 6). Primer P3 is complementary to the 5'-terminus region of the araE gene which is also present in the hybrid $P_{L\text{-}tac}$ promoter (SEQ ID NO: 3).

The amplified DNA fragment can be purified by agarose gel-electrophoresis, extracted using "GenElute Spin Columns" (Sigma, USA) and precipitated by ethanol. The obtained DNA fragment can be used for electroporation and Red-mediated integration into the bacterial chromosome of the *E. coli* MG1655/pKD46.

MG1655/pKD46 cells can be grown overnight at 30° C. in liquid LB-medium with the addition of ampicillin (100 µg/ml), then diluted 1:100 with SOB-medium (Yeast extract, 5 g/l; NaCl, 0.5 g/l; Tryptone, 20 g/l; KCl, 2.5 mM; $MgCl_2$, 10 mM), with the addition of ampicillin (100 µg/ml) and L-arabinose (10 mM) (arabinose is used for inducing the plasmid encoding genes of the Red system) and grown at 30° C. to reach the optical density of the bacterial culture $OD_{600}$=0.4-0.7. Grown cells from 10 ml of the bacterial culture are washed 3 times with ice-cold de-ionized water, followed by suspending in 100 µl of the water. 10 µl of DNA fragment (100 ng) dissolved in the de-ionized water is added to the cell suspension. The electroporation can be performed by "Bio-Rad" electroporator (USA) (No. 165-2098, version 2-89) according to the manufacturer's instructions. Shocked cells are added to 1-ml of SOC medium (Sambrook et al, "Molecular Cloning A Laboratory Manual, Second Edition", Cold Spring Harbor Laboratory Press (1989)), incubated 2 hours at 37° C., and then are spread onto L-agar containing 25 µg/ml of chloramphenicol. Colonies grown within 24 hours can be tested for the presence of $Cm^R$ marker, instead of the native promoter region of the araE gene by PCR using primers P4 (SEQ ID NO: 7) and P5 (SEQ ID NO: 8). For this purpose, a freshly isolated colony can be suspended in 20 µl water and then 1 µl of obtained suspension can be used for PCR. The following temperature profile can be used: initial DNA denaturation at 95° C. for 10 min; then 30 cycles of denaturation at 95° C. for 30 sec, annealing at 55° C. for 30 sec and elongation at 72° C. for 1 min; the final elongation at 72° C. for 7 min. $Cm^R$ colonies should contain the desired ~1400 bp DNA fragment, confirming the presence of $Cm^R$ marker DNA instead of 45 bp native promoter region of araE gene (see FIG. 1). One of these strains can be cured from the thermosensitive plasmid pKD46 by culturing at 37° C. and the resulting strain can be named as *E. coli* MG1655$P_{L\text{-}tac}$araE.

Example 2

Effect of Increasing the araE Gene Expression on L-threonine Production

To test the effect of enhanced expression of the araE gene under the control Of $P_{L\text{-}tac}$ promoter on threonine production, DNA fragments from the chromosome of the above-described *E. coli* MG1655$P_{L\text{-}tac}$araE can be transferred to the threonine-producing *E. coli* strain VKPM B-3996 by P1 transduction (Miller, J. H. (1972) Experiments in Molecular Genetics, Cold Spring Harbor Lab. Press, Plainview, N.Y.).

Both *E. coli* strains B-3996 and B-3996$P_{L\text{-}tac}$araE can be grown for 18-24 hours at 37° C. on L-agar plates. To obtain a seed culture, the strain can be grown on a rotary shaker (250 rpm) at 32° C. for 18 hours in 20×200 mm test tubes containing 2 ml of L-broth with 4% sucrose. Then, the fermentation medium can be inoculated with 0.21 ml (10%) seed material. The fermentation can be performed in 2 ml of minimal medium for fermentation in 20×200 mm test tubes. Cells can be grown for 48 hours at 32° C. with shaking at 250 rpm.

After cultivation, the amount of accumulated L-threonine in the medium can be determined by paper chromatography using the following mobile phase: butanol: acetic acid:water=4:1:1 (v/v). A solution (2%) of ninhydrin in acetone can be used as a visualizing reagent. A spot containing L-threonine can be cut off, L-threonine can be eluted in 0.5% water solution of $CdCl_2$, and the amount of L-threonine can be estimated spectrophotometrically at 540 nm.

The composition of the fermentation medium (g/l) is as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4\,7H_2O$ | 0.8 |
| $FeSO_4\,7H_2O$ | 0.02 |
| $MnSO_4\,5H_2O$ | 0.02 |
| Thiamine HCl | 0.0002 |
| Yeast extract | 1.0 |
| $CaCO_3$ | 30.0 |

Glucose and magnesium sulfate are sterilized separately. $CaCO_3$ is dry-heat sterilized at 180° C. for 2 hours. The pH is adjusted to 7.0. Antibiotic is introduced into the medium after sterilization.

Example 3

Effect of Increasing the araE Gene Expression on L-lysine Production (1)

To test the effect of enhanced expression of the araE gene under the control Of $P_{L-tac}$ promoter on lysine production, DNA fragments from the chromosome of the above-described *E. coli* MG1655$P_{L-tac}$araE can be transferred to the lysine-producing *E. coli* strain WC196 (pCABD2) by P1 transduction (Miller, J. H. (1972) Experiments in Molecular Genetics, Cold Spring Harbor Lab. Press, Plainview, N.Y.). pCABD2 is a plasmid comprising a dapA gene coding for a dihydrodipicolinate synthase having a mutation which desensitizes feedback inhibition by L-lysine, a lysC gene coding for aspartokinase III having a mutation which desensitizes feedback inhibition by L-lysine, a dapB gene coding for a dihydrodipicolinate reductase gene, and a ddh gene coding for diaminopimelate dehydrogenase (U.S. Pat. No. 6,040,160).

Both *E coli* strains WC196(pCABD2) and WC196 (pCABD2)$P_{L-tac}$araE can be cultured in the L-medium containing 20 mg/l of streptomycin at 37° C., and 0.3 ml of the obtained culture can be inoculated into 20 ml of the fermentation medium containing the required drugs in a 500 ml-flask. The cultivation can be carried out at 37° C. for 16 hours by using a reciprocal shaker at the agitation speed of 115 rpm. After the cultivation, the amounts of L-lysine and residual glucose in the medium can be measured by a known method (Biotech-analyzer AS210, manufactured by Sakura Seiki Co.). Then, the yield of L-lysine relative to consumed glucose can be calculated for each of the strains.

The composition of the fermentation medium (g/l) is as follows:

| | |
|---|---|
| Glucose | 40 |
| $(NH_4)_2SO_4$ | 24 |
| $K_2HPO_4$ | 1.0 |
| $MgSO_4 \times 7H_2O$ | 1.0 |
| $FeSO_4 \times 7H_2O$ | 0.01 |
| $MnSO_4 \times 5H_2O$ | 0.01 |
| Yeast extract | 2.0 | pH is adjusted to 7.0 by KOH and the medium is autoclaved at 115° C. for 10 min. Glucose and $MgSO_4 \times 7H_2O$ are sterilized separately. 30 g/l of $CaCO_3$, which has been dry-heat sterilized at 180° C. for 2 hours, is added.

Example 4

Effect of Increasing the araE Gene Expression on L-histidine Production

To test the effect of enhanced expression of the araE gene under the control Of $P_{L-tac}$ promoter on arginine production, DNA fragments from the chromosome of the above-described *E. coli* MG1655$P_{L-tac}$araE can be transferred to the histidine-producing *E. coli* strain 80 by P1 transduction (Miller, J. H. (1972) Experiments in Molecular Genetics, Cold Spring Harbor Lab. Press, Plainview, N.Y.). The strain 80 has been described in Russian patent 2119536 and deposited in the Russian National Collection of Industrial Microorganisms (Russia, 113545 Moscow, 1st Dorozhny proezd, 1) under accession number VRPM B-7270.

The resulting strain 80 $P_{L-tac}$araE and parent strain 80 can each be cultivated in L broth for 6 hours at 29° C. Then, 0.1 ml of obtained culture can be inoculated into 2 ml of fermentation medium in 20×200 mm test tube and cultivated for 65 hours at 29° C. with a rotary shaker (350 rpm). After cultivation, the amount of histidine which has accumulated in the medium can be determined by paper chromatography. The paper can be developed with a mobile phase: n-butanol:acetic acid:water=4:1:1 (v/v). A solution of ninhydrin (0.5%) in acetone can be used as a visualizing reagent.

The composition of the fermentation medium (pH 6.0) (g/l):

| | |
|---|---|
| Glucose | 100.0 |
| Mameno(soybean hydrolysate) | 0.2 as total nitrogen |
| L-proline | 1.0 |
| $(NH_4)_2SO_4$ | 25.0 |
| $KH_2PO_4$ | 2.0 |
| $MgSO_4 \times 7H_2O$ | 1.0 |
| $FeSO_4 \times 7H_2O$ | 0.01 |
| $MnSO_4$ | 0.01 |
| Thiamine | 0.001 |
| Betaine | 2.0 |
| $CaCO_3$ | 60.0 |

Glucose, proline, betaine and $CaCO_3$ are sterilized separately. pH is adjusted to 6.0 before sterilization.

Example 5

Effect of Increasing the araE Gene Expression on L-phenylalanine Production

To test the effect of enhanced expression of the araE gene under the control Of $P_{L-tac}$ promoter on phenylalanine production, DNA fragments from the chromosome of the above-described E. coli MG1655P$_{L-tac}$araE can be transferred to phenylalanine-producing E. coli strain AJ12739 by P1 transduction (Miller, J. H. (1972) Experiments in Molecular Genetics, Cold Spring Harbor Lab. Press, Plainview, N.Y.). The strain AJ12739 has been deposited in the Russian National Collection of Industrial Microorganisms (VKPM) (Russia, 113545 Moscow, 1$^{st}$ Dorozhny proezd, 1) on Nov. 6, 2001 under accession number VKPM B-8197.

The resulting strain AJ12739 P$_{L-tac}$araE and parent strain AJ12739 can each be cultivated at 37° C. for 18 hours in a nutrient broth, and 0.3 ml of the obtained culture can be inoculated into 3 ml of a fermentation medium in a 20×200 mm test tube and cultivated at 37° C. for 48 hours with a rotary shaker. After cultivation, the amount of phenylalanine which has accumulated in the medium can be determined by TLC. 10×15 cm TLC plates coated with 0.11 mm layers of Sorbfil silica gel without fluorescent indicator (Stock Company Sorbpolymer, Krasnodar, Russia) can be used. Sorbfil plates can be developed with a mobile phase: propan-2-ol:ethylacetate:25% aqueous ammonia:water=40:40:7:16 (v/v). A solution (2%) of ninhydrin in acetone can be used as a visualizing reagent.

The composition of the fermentation medium (g/l):

| | |
|---|---|
| Glucose | 40.0 |
| (NH$_4$)$_2$SO$_4$ | 16.0 |
| K$_2$HPO$_4$ | 0.1 |
| MgSO$_4$ × 7H$_2$O | 1.0 |
| FeSO$_4$ × 7H$_2$O | 0.01 |
| MnSO$_4$ × 5H$_2$O | 0.01 |
| Thiamine HCl | 0.0002 |
| Yeast extract | 2.0 |
| Tyrosine | 0.125 |
| CaCO$_3$ | 20.0 |

Glucose and magnesium sulfate are sterilized separately. CaCO$_3$ is dry-heat sterilized at 180° for 2 hours. pH is adjusted to 7.0.

Example 6

Effect of Increasing the araE Gene Expression on L-arginine Production

To test the effect of enhanced expression of the araE gene which is under the control of P$_{L-tac}$ promoter on arginine production, DNA fragments from the chromosome of the above-described E. coli MG1655P$_{L-tac}$araE can be transferred to arginine-producing E. coli strain 382 by P1 transduction (Miller, J. H. (1972) Experiments in Molecular Genetics, Cold Spring Harbor Lab. Press, Plainview, N.Y.). The strain 382 has been deposited in the Russian National Collection of Industrial Microorganisms (VKPM) (Russia, 117545 Moscow, 1$^{st}$ Dorozhny proezd, 1) on Apr. 10, 2000 under accession number VKPM B-7926.

The resulting strain 382 P$_{L-tac}$araE and parent strain 382 can be each cultivated at 32° C. for 18 hours in 2 ml of LB nutrient broth, and 0.3 ml of the obtained culture can be inoculated into 2 ml of fermentation medium in a 20×200 mm test tube, and cultivated at 32° C. for 48 hours on a rotary shaker.

After the cultivation, the amount of L-arginine which has accumulated in the medium can be determined by paper chromatography using following mobile phase: butanol: acetic acid:water=4:1:1 (v/v). A solution (2%) of ninhydrin in acetone can be used as a visualizing reagent. A spot containing L-arginine can be cut off, L-arginine can be eluted in 0.5% water solution of CdCl$_2$, and the amount of L-arginine can be estimated spectrophotometrically at 540 nm.

The composition of the fermentation medium (g/l):

| | |
|---|---|
| Glucose | 48.0 |
| (NH4)$_2$SO$_4$ | 35.0 |
| KH$_2$PO$_4$ | 2.0 |
| MgSO$_4$ × 7H$_2$O | 1.0 |
| Thiamine HCl | 0.0002 |
| Yeast extract | 1.0 |
| L-isoleucine | 0.1 |
| CaCO3 | 5.0 |

Glucose and magnesium sulfate are sterilized separately. CaCO$_3$ is dry-heat sterilized at 180° C. for 2 hours. pH is adjusted to 7.0.

Example 7

Effect of Increasing the araE Gene Expression on L-tryptophan Production

To test the effect of enhanced expression of the araE gene under the control Of P$_{L-tac}$ promoter on tryptophan production, DNA fragments from the chromosome of the above-described E. coli MG1655P$_{L-tac}$araE can be transferred to tryptophan-producing E. coli strain SV164 (pGH5) by P1 transduction (Miller, J. H. (1972) Experiments in Molecular Genetics, Cold Spring Harbor Lab. Press, Plainview, N.Y.). The strain SV164 (pGH5) is described in detail in U.S. Pat. No. 6,180,373 or European patent 0662143.

The resulting strain SV164(pGH5) P$_{L-tac}$araE and parent strain SV164(pGH5) can each be cultivated with shaking at 37° C. for 18 hours in a 3 ml of nutrient broth supplemented with 20 mg/ml of tetracycline (marker of pGH5 plasmid). 0.3 ml of the obtained cultures can be inoculated into 3 ml of a fermentation medium containing tetracycline (20 mg/ml) in 20×200 mm test tubes, and cultivated at 37° C. for 48 hours with a rotary shaker at 250 rpm. After cultivation, the amount of tryptophan which has accumulated in the medium can be determined by TLC as described in Example 5.

The composition of the fermentation medium is presented in Table 1.

TABLE 1

| Groups | Component | Final concentration, g/l |
|---|---|---|
| A | KH$_2$PO$_4$ | 1.5 |
| | NaCl | 0.5 |
| | (NH$_4$)$_2$SO$_4$ | 1.5 |
| | L-Methionine | 0.05 |
| | L-Phenylalanine | 0.1 |
| | L-Tyrosine | 0.1 |
| | Mameno (total N) | 0.07 |
| B | Glucose | 40.0 |
| | MgSO$_4$ × 7H$_2$O | 0.3 |
| C | CaCl$_2$ | 0.011 |
| D | FeSO$_4$ × 7H$_2$O | 0.075 |
| | Sodium citrate | 1.0 |
| E | Na$_2$MoO$_4$ × 2H$_2$O | 0.00015 |
| | H$_3$BO$_3$ | 0.0025 |
| | CoCl$_2$ × 6H$_2$O | 0.00007 |
| | CuSO$_4$ × 5H$_2$O | 0.00025 |
| | MnCl$_2$ × 4H$_2$O | 0.0016 |
| | ZnSO$_4$ × 7H$_2$O | 0.0003 |
| F | Thiamine HCl | 0.005 |
| G | CaCO$_3$ | 30.0 |
| H | Pyridoxine | 0.03 |

Group A has pH 7.1 adjusted by NH$_4$OH. Each group is sterilized separately.

Example 8

Effect of Increasing the araE Gene Expression on L-glutamic Acid Production

To test the effect of enhanced expression of the araE gene under the control Of $P_{L-tac}$ promoter on glutamic acid production, DNA fragments from the chromosome of the above-described *E. coli* MG1655$P_{L-tac}$araE can be transferred to glutamic acid-producing *E. coli* strain VL334thrC$^+$ by P1 transduction (Miller, J. H. (1972) Experiments in Molecular Genetics, Cold Spring Harbor Lab. Press, Plainview, N.Y.). The strain VL334thrC$^+$ is described in detail in European patent application EP 1172433.

The resulting strain VL334thrC$^+$ $P_{L-tac}$araE and parent strain VL334thrC$^+$ can each be cultivated with shaking at 37° C. for 18 hours in a 3 ml of nutrient broth. 0.3 ml of the obtained cultures can be inoculated into 3 ml of a fermentation medium in 20×200 mm test tubes, and cultivated at 37° C. for 48 hours with a rotary shaker at 250 rpm.

The composition of the fermentation medium (pH 7.2) (g/l):

| | |
|---|---|
| Glucose | 60.0 |
| Ammonium sulfate | 25.0 |
| KH$_2$PO$_4$ | 2.0 |
| MgSO$_4$ | 1.0 |
| Thiamine | 0.0001 |
| L-isoleucine | 0.05 |
| CaCO$_3$ | 25.0 |

Glucose and CaCO$_3$ are sterilized separately.

Example 9

Effect of Increasing the araE Gene Expression on L-lysine Production (2)

(1) Construction of an L-lysine Producing Strain in which Lysine Decarboxylase Genes are Disrupted

*E. coli* has lysine decarboxylases which are encoded by the cadA gene (Genbank Accession No. NP_418555) and the 1dcC gene (Genbank Accession No. NP_414728) (see WO96/17930). *E. coli* WC196 (FERM BP-5252) was employed as the parent strain, and a strain in which the genes encoding lysine decarboxylases are disrupted was first constructed by the method known as "Red-driven integration", initially developed by Datsenko and Wanner (Proc. Natl. Acad. Sci. USA, 97, No. 12, 6640-6645 (2000)) and a λ phage-derived excision system (Cho E. H. et al, J. Bacteriol., 184 (18): 5200-3 (2002)). "Red-driven integration" makes it possible to construct a gene-disrupted strain in one step by employing a PCR product obtained by using as primers synthetic oligonucleotides designed to have a part of the targeted gene on the 5'-ends and a part of an antibiotic-resistance gene on the 3'-ends. Combining the λ phage-derived excision system permits the removal of the antibiotic-resistance gene that has been incorporated into the gene-disrupted strain (JP 2005-058227A).

The cadA gene was disrupted as follows. The plasmid pMW118-attL-Cm-attR (JP 2005-058227A) was employed as the PCR template. pMW118-attL-Cm-attR is a plasmid obtained by inserting attL and attR genes, which are λ phage attachment sites, and the cat gene, an antibiotic-resistance gene, into pMW118 (Takara Bio) in the order attL-cat-attR. PCR was conducted using primers P6 (SEQ ID NO: 9) and P7 (SEQ ID NO: 10) having sequences corresponding to attL and attR on the 3'-terminals and a sequence corresponding to a part of the targeted cadA gene on the 5'-terminals. The amplified PCR product was purified with agarose gel and introduced by electroporation into *E. coli* WC196 comprising the plasmid pKD46 having a temperature-sensitive replication capability. The plasmid pKD46 (Proc. Natl. Acad. Sci. USA, 97, No. 12, 6640-6645 (2000)) contains a DNA fragment with a total of 2,154 bases of λ phage containing genes (γ, β, and exo genes) encoding the Red recombinase of the λ Red homologous recombination system regulated by the arabinose-induced ParaB promoter (GenBank/EMBL accession number J02459, base nos. 31088 to 33241). The plasmid pKD46 is necessary to incorporate the PCR product into the chromosome of *E. coli* WC196.

The competent cells employed in electroporation were prepared as follows. *E. coli* WC196 that had been cultured overnight at 30° C. in the LB medium containing 100 mg/l of ampicillin was diluted 100-fold in 5 ml of the SOB medium containing ampicillin (20 mg/L) and L-arabinose (1 mM) (Molecular Cloning: Laboratory Manual, 2$^{nd}$ Ed., Sambrook, J. et al., Cold Spring Harbor Laboratory Press (1989)). The diluted product obtained was grown with aeration at 30° C. until OD$_{600}$ reached approximately 0.6, concentrated 100-fold, and washed three times with 10 percent glycerol in preparation for electroporation. The electroporation was conducted with 70 μl of competent cells and about 100 ng of the PCR product. Following the electroporation, 1 ml of the SOC medium (Molecular Cloning: Laboratory Manual, 2$^{nd}$ Ed., Sambrook, J. et al., Cold Spring Harbor Laboratory Press (1989)) was added and the cells were cultured at 37° C. for 2.5 hours. They were then cultured on the L-agar plate medium containing chloramphenicol (Cm) (25 mg/L) at 37° C. and Cm-resistant recombinants were selected. Then, to remove the pKD46 plasmid, the cells were subjected to subculture twice at 42° C. on the L-agar medium containing Cm, the ampicillin resistance of the colonies obtained was tested, and the ampicillin-sensitive strains that had lost pKD46 were collected. The deletion of the cadA gene in variants identified based on the chloramphenicol resistance gene were confirmed by PCR. The cadA-deficient strain obtained was named WC196ΔcadA::att-cat.

Next, to remove the att-cat genes introduced into the cadA gene, pMW-intxis-ts was employed as a helper plasmid (JP 2005-058227A). pMW-intxis-ts is a plasmid that carries genes encoding excisionase (Xis) and integrase (Int) of λ phage and has a temperature-sensitive replication capability. Competent cells of the WC196ΔcadA::att-cat strain obtained as stated above were prepared by the usual methods, transformed with the helper plasmid pMW-intxis-ts, and cultured on L-agar plate medium containing 50 mg/L of ampicillin at 30° C. to select the strains with resistance to ampicillin. Next, to remove the pMW-intxis-ts plasmid, two generations were cultivated on the L-agar plate medium at 42° C. The resistance to ampicillin and chloramphenicol of the colonies obtained was tested and a chloramphenicol and ampicillin-sensitive was obtained. This strain is a cadA-disrupted strain in which att-cat and pMW-intxis-ts are eliminated, and was named WC196ΔcadA.

Then the 1dcC gene in WC196ΔcadA was deleted by using primers P8 (SEQ ID NO: 11) and P9 (SEQ ID NO: 12) according to the above-described method. Thus a cadA and 1dcC-disrupted strain was obtained and named WC196ΔcadAΔ1dcC.

WC196ΔcadAΔ1dcC was transformed by the usual method using the plasmid pCABD2 (WO01/53459). pCABD2 is a plasmid comprising a dapA gene coding for a dihydrodipicolinate synthase having a mutation which desensitizes feedback inhibition by L-lysine, a lysC gene coding for aspartokinase III having a mutation which desensitizes feedback inhibition by L-lysine, a dapB gene coding for a dihydrodipicolinate reductase gene, and a ddh gene coding for diaminopimelate dehydrogenase (U.S. Pat. No. 6,040,160). Thus the lysine-producing strain WC196ΔcadAΔ1dcC/pCABD2 (WC196LC (pCABD2)) was constructed.

(2) Effect of Increasing the araE Gene Expression on L-lysine Production.

To test the effect of enhanced expression of the araE gene under the control of $P_{lac}$ promoter on lysine production, a DNA fragment comprising the araE gene was cloned into pMW219 (Takara Shuzo, Japan). Specific procedures of constructing a plasmid for enhancing expression of the araE gene were as follows; DNA fragments comprising the araE gene were amplified by PCR method, using the pair of primers P10 (SEQ ID NO: 13) and P11 (SEQ ID NO: 14), which included the KpnI and SacI sites, respectively. PCR was performed using the "Pyrobest DNA Polymerase" (Applied Takara Shuzo). Approximately 20 ng of the genomic DNA of E. coli K-12 MG1655 was used as a template DNA for the PCR amplification. The temperature profile was the following: initial DNA denaturation at 94° C. for 1 min, followed by 30 cycles of denaturation at 98° C. for 5 sec, annealing at 59° C. for 30 sec, elongation at 72° C. for 2 min; and the final elongation at 72° C. for 10 min. Then, the amplified DNA fragments were purified by agarose gel-electrophoresis, extracted using "GenElute Spin Columns" (Sigma, USA) and precipitated by ethanol. The PCR product and the vector pMW219 were digested by KpnI and SacI, and then ligated to each other by 2×Ligation Kit (Nippon Gene). Thus the plasmid pM-araE containing the araE gene under the control of the $P_{lac}$ promoter was constructed.

The lysine-producing E. coli strain WC196LC (pCABD2) was transformed with pMW219 for a control and pM-araE, and WC196LC (pCABD2, pMW219) and WC196LC (pCABD2, pM-araE) were constructed, respectively.

Both E. coli strains WC196LC (pCABD2, pMW219) and WC196LC (pCABD2, pM-araE) were cultured in the L-medium containing 25 mg/l of kanamycin and 20 mg/l of streptomycin at 37° C. until $OD_{600}$ reached approximately 0.6. Then, an equal volume of 40% glycerol solution was added to each culture broth, stirred, and then divided into appropriate volumes, and stored at −80° C. These are referred to herein as glycerol stocks.

The glycerol stocks of these strains were thawed, and 100 µl of each stock was uniformly plated on an L-plate containing 25 mg/l of kanamycin and 20 mg/l of streptomycin and incubated at 37° C. for 24 hours. About ⅛ of the cells collected from the plate were inoculated into 20 ml of the fermentation medium containing 25 mg/l of kanamycin and 20 mg/l of streptomycin in a 500 ml Sakaguchi flask, and cultured at 37° C. for 16 hours on a culturing apparatus with shaking by reciprocal movement. After cultivation, the amount of lysine which had accumulated in the medium was measured using Biotech Analyzer AS210 (Sakura Seiki). The composition of the fermentation medium (g/l) is as follows:

| | |
|---|---|
| Glucose | 40 |
| $(NH_4)_2SO_4$ | 24 |
| $K_2HPO_4$ | 1.0 |
| $MgSO_4 \times 7H_2O$ | 1.0 |
| $FeSO_4 \times 7H_2O$ | 0.01 |
| $MnSO_4 \times 5H_2O$ | 0.01 |
| Yeast extract | 2.0 | pH was adjusted to 7.0 by KOH and the medium was autoclaved at 115° C. for 10 min. Glucose and $MgSO_4 \times 7H_2O$ were sterilized separately. 30 g/l of $CaCO_3$, which had been dry-heat sterilized at 180° C. for 2 hours, was added.

It can be seen from the Table 2, E. coli WC196LC (pCABD2, pM-araE) causes a higher amount of L-lysine accumulation as compared with E. coli WC196LC (pCABD2, pMW219).

TABLE 2

| Strain | $OD_{600}$ | Lys · HCl, g/l |
|---|---|---|
| WC196LC(pCABD2, pMW219) | 6.5 | 3.8 |
| WC196LC(pCABD2, pM-araE) | 9.6 | 5.4 |

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

We claim:

1. A method for producing an L-amino acid comprising cultivating an L-amino acid-producing *E. coli* bacterium in a culture medium which contains glucose as a carbon source to cause accumulation of the L-amino acid in the culture medium, and isolating the L-amino acid from the culture medium, wherein said bacterium has been modified to enhance an activity of L-arabinose permease as compared to a wild strain, by placing a gene encoding L-arabinose permease under the control of a potent promoter, wherein said gene encoding L-arabinose permease comprises a DNA selected from the group consisting of:

(a) a DNA comprising nucleotides 1 to 1419 in SEQ ID NO: 1, and (b) a DNA which is hybridizable with nucleotides 1-1419 in SEQ ID NO: 1 under stringent conditions, and wherein said DNA encodes a protein having an activity of L-arabinose permease and having a homology of not less than 95% with respect to the entire amino acid sequence of SEQ ID NO: 2, and wherein said stringent conditions comprise washing at 60° C. at a salt concentration of 0.1×SSC and 0.1% SDS, for approximately 15 minutes.

2. The method according to claim 1, wherein said L-amino acid is L-threonine.

3. The method according to claim 1, wherein said L-amino acid is L-lysine.

4. The method according to claim 1, wherein said L-amino acid is L-histidine.

5. The method according to claim 1, wherein said L-amino acid is L-phenylalanine.

6. The method according to claim 1, wherein said L-amino acid is L-arginine.

7. The method according to claim 1, wherein said L-amino acid is L-tryptophan.

8. The method according to claim 1, wherein said L-amino acid is L-glutamic acid.

9. The method according to claim 1, wherein said bacterium has been additionally modified to enhance activity of glucokinase by increasing the copy number of the gene encoding glucokinase or by modifying an expression control sequence of the gene encoding glucokinase.

10. The method according to claim 1, where said bacterium has been additionally modified to enhance an activity of xylose isomerase by increasing the copy number of the gene encoding xylose isomerase or by modifying an expression control sequence of the gene encoding xylose isomerase.

11. The method according to claim 1, wherein said gene encoding L-arabinose permease is isolated from *E. coli*.

12. The method according to claim 2, wherein said bacterium has been further modified to enhance expression of a gene selected from the group consisting of
- a mutant thrA gene which codes for aspartokinase homoserine dehydrogenase I and is resistant to feedback inhibition by threonine,
- the thrB gene which codes for homoserine kinase,
- the thrC gene which codes for threonine synthase,
- the rhtA gene which codes for a putative transmembrane protein,
- the asd gene which codes for aspartate-β-semialdehyde dehydrogenase,
- the aspC gene which codes for aspartate aminotransferase (aspartate transaminase), and
- combinations thereof,
- wherein said expression of said gene is enhanced by increasing the copy number of the gene or by modifying an expression control sequence of the gene.

13. The method according to claim 12, wherein said bacterium has been modified to increase expression of said mutant thrA gene, said thrB gene, said thrC gene, and said rhtA gene.

14. A method for producing an L-amino acid comprising cultivating an L-amino acid-producing *Escherichia coli* in a culture medium which contains glucose as a carbon source so to cause accumulation of the L-amino acid in the culture medium, and isolating the L-amino acid from the culture medium,
wherein a vector is introduced into said *Escherichia coli*, and wherein said vector comprises a DNA selected from the group consisting of:
(a) a DNA comprising nucleotides 1 to 1419 in SEQ ID NO: 1, and
(b) a DNA which hybridizes with nucleotides 1 to 1419 in SEQ ID NO: 1 under stringent conditions, and encodes a protein having an activity of L-arabinose permease, and having a homology of not less than 95% with respect to the entire amino acid sequence of SEQ ID NO: 2, and
wherein said stringent conditions comprises washing at 60° C. at a salt concentration of 0.1×SSC and 0.1% SDS, for approximately 15 minutes.

15. The method according to claim 14, wherein said L-amino acid is L-threonine.

16. The method according to claim 14, wherein said L-amino acid is L-lysine.

17. The method according to claim 14, wherein said L-amino acid is L-histidine.

18. The method according to claim 14, wherein said L-amino acid is L-phenylalanine.

19. The method according to claim 14, wherein said L-amino acid is L-arginine.

20. The method according to claim 14, wherein said L-amino acid is L-tryptophan.

21. The method according to claim 14, wherein said L-amino acid is L-glutamic acid.

22. The method according to claim 14, wherein said bacterium has been additionally modified to enhance an activity of glucokinase by increasing the copy number of the gene encoding glucokinase or by modifying an expression control sequence of the gene encoding glucokinase.

23. The method according to claim 14, where said bacterium has been additionally modified to enhance an activity of xylose isomerase by increasing the copy number of the gene encoding xylose isomerase or by modifying an expression control sequence of the gene encoding xylose isomerase.

24. The method according to claim 14, wherein said gene encoding L-arabinose permease is isolated from *E. coli*.

* * * * *

SEQUENCE LISTING

```
<160> NUMBER OF SEQ ID NOS: 14

<210> SEQ ID NO 1
<211> LENGTH: 1419
<212> TYPE: DNA
<213> ORGANISM: Escherichia coli
<220> FEATURE:
<221> NAME/KEY: CDS
<222> LOCATION: (1)..(1419)

<400> SEQUENCE: 1 atg gtt act atc aat acg gaa tct gct tta acg cca cgt tct ttg cgg       48
Met Val Thr Ile Asn Thr Glu Ser Ala Leu Thr Pro Arg Ser Leu Arg
1               5                   10                  15 gat acg cgg cgt atg aat atg ttt gtt tcg gta gct gct gcg gtc gca       96
```

```
              Asp Thr Arg Arg Met Asn Met Phe Val Ser Val Ala Ala Val Ala
                           20                  25                  30 gga ttg tta ttt ggt ctt gat atc ggc gta atc gcc gga gcg ttg ccg           144
Gly Leu Leu Phe Gly Leu Asp Ile Gly Val Ile Ala Gly Ala Leu Pro
             35                  40                  45 ttc att acc gat cac ttt gtg ctg acc agt cgt ttg cag gaa tgg gtg           192
Phe Ile Thr Asp His Phe Val Leu Thr Ser Arg Leu Gln Glu Trp Val
 50                  55                  60 gtt agt agc atg atg ctc ggt gca gca att ggt gcg ctg ttt aat ggt           240
Val Ser Ser Met Met Leu Gly Ala Ala Ile Gly Ala Leu Phe Asn Gly
 65                  70                  75                  80 tgg ctg tcg ttc cgc ctg ggg cgt aaa tac agc ctg atg gcg ggg gcc           288
Trp Leu Ser Phe Arg Leu Gly Arg Lys Tyr Ser Leu Met Ala Gly Ala
                 85                  90                  95 atc ctg ttt gta ctc ggt tct ata ggg tcc gct ttt gcg acc agc gta           336
Ile Leu Phe Val Leu Gly Ser Ile Gly Ser Ala Phe Ala Thr Ser Val
            100                 105                 110 gag atg tta atc gcc gct cgt gtg gtg ctg ggc att gct gtc ggg atc           384
Glu Met Leu Ile Ala Ala Arg Val Val Leu Gly Ile Ala Val Gly Ile
        115                 120                 125 gcg tct tac acc gct cct ctg tat ctt tct gaa atg gca agt gaa aac           432
Ala Ser Tyr Thr Ala Pro Leu Tyr Leu Ser Glu Met Ala Ser Glu Asn
    130                 135                 140 gtt cgc ggt aag atg atc agt atg tac cag ttg atg gtc aca ctc ggc           480
Val Arg Gly Lys Met Ile Ser Met Tyr Gln Leu Met Val Thr Leu Gly
145                 150                 155                 160 atc gtg ctg gcg ttt tta tcc gat aca gcg ttc agt tat agc ggt aac           528
Ile Val Leu Ala Phe Leu Ser Asp Thr Ala Phe Ser Tyr Ser Gly Asn
                165                 170                 175 tgg cgc gca atg ttg ggg gtt ctt gct tta cca gca gtt ctg ctg att           576
Trp Arg Ala Met Leu Gly Val Leu Ala Leu Pro Ala Val Leu Leu Ile
            180                 185                 190 att ctg gta gtc ttc ctg cca aat agc ccg cgc tgg ctg gcg gaa aag           624
Ile Leu Val Val Phe Leu Pro Asn Ser Pro Arg Trp Leu Ala Glu Lys
        195                 200                 205 ggg cgt cat att gag gcg gaa gaa gta ttg cgt atg ctg cgc gat acg           672
Gly Arg His Ile Glu Ala Glu Glu Val Leu Arg Met Leu Arg Asp Thr
    210                 215                 220 tcg gaa aaa gcg cga gaa gaa ctc aac gaa att cgt gaa agc ctg aag           720
Ser Glu Lys Ala Arg Glu Glu Leu Asn Glu Ile Arg Glu Ser Leu Lys
225                 230                 235                 240 tta aaa cag ggc ggt tgg gca ctg ttt aag atc aac cgt aac gtc cgt           768
Leu Lys Gln Gly Gly Trp Ala Leu Phe Lys Ile Asn Arg Asn Val Arg
                245                 250                 255 cgt gct gtg ttt ctc ggt atg ttg ttg cag gcg atg cag cag ttt acc           816
Arg Ala Val Phe Leu Gly Met Leu Leu Gln Ala Met Gln Gln Phe Thr
            260                 265                 270 ggt atg aac atc atc atg tac tac gcg ccg cgt atc ttc aaa atg gcg           864
Gly Met Asn Ile Ile Met Tyr Tyr Ala Pro Arg Ile Phe Lys Met Ala
        275                 280                 285 ggc ttt acg acc aca gaa caa cag atg att gcg act ctg gtc gta ggg           912
Gly Phe Thr Thr Thr Glu Gln Gln Met Ile Ala Thr Leu Val Val Gly
    290                 295                 300 ctg acc ttt atg ttc gcc acc ttt att gcg gtg ttt acg gta gat aaa           960
Leu Thr Phe Met Phe Ala Thr Phe Ile Ala Val Phe Thr Val Asp Lys
305                 310                 315                 320 gca ggg cgt aaa ccg gct ctg aaa att ggt ttc agc gtg atg gcg tta          1008
Ala Gly Arg Lys Pro Ala Leu Lys Ile Gly Phe Ser Val Met Ala Leu
                325                 330                 335
```

-continued

```
ggc act ctg gtg ctg ggc tat tgc ctg atg cag ttt gat aac ggt acg    1056
Gly Thr Leu Val Leu Gly Tyr Cys Leu Met Gln Phe Asp Asn Gly Thr
        340                 345                 350 gct tcc agt ggc ttg tcc tgg ctc tct gtt ggc atg acg atg atg tgt    1104
Ala Ser Ser Gly Leu Ser Trp Leu Ser Val Gly Met Thr Met Met Cys
355                 360                 365 att gcc ggt tat gcg atg agc gcc gcg cca gtg gtg tgg atc ctg tgc    1152
Ile Ala Gly Tyr Ala Met Ser Ala Ala Pro Val Val Trp Ile Leu Cys
    370                 375                 380 tct gaa att cag ccg ctg aaa tgc cgc gat ttc ggt att acc tgt tcg    1200
Ser Glu Ile Gln Pro Leu Lys Cys Arg Asp Phe Gly Ile Thr Cys Ser
385                 390                 395                 400 acc acc acg aac tgg gtg tcg aat atg att atc ggc gcg acc ttc ctg    1248
Thr Thr Thr Asn Trp Val Ser Asn Met Ile Ile Gly Ala Thr Phe Leu
                405                 410                 415 aca ctg ctt gat agc att ggc gct gcc ggt acg ttc tgg ctc tac act    1296
Thr Leu Leu Asp Ser Ile Gly Ala Ala Gly Thr Phe Trp Leu Tyr Thr
            420                 425                 430 gcg ctg aac att gcg ttt gtg ggc att act ttc tgg ctc att ccg gaa    1344
Ala Leu Asn Ile Ala Phe Val Gly Ile Thr Phe Trp Leu Ile Pro Glu
        435                 440                 445 acc aaa aat gtc acg ctg gaa cat atc gaa cgc aaa ctg atg gca ggc    1392
Thr Lys Asn Val Thr Leu Glu His Ile Glu Arg Lys Leu Met Ala Gly
    450                 455                 460 gag aag ttg aga aat atc ggc gtc tga                                1419
Glu Lys Leu Arg Asn Ile Gly Val
465                 470

<210> SEQ ID NO 2
<211> LENGTH: 472
<212> TYPE: PRT
<213> ORGANISM: Escherichia coli

<400> SEQUENCE: 2

Met Val Thr Ile Asn Thr Glu Ser Ala Leu Thr Pro Arg Ser Leu Arg
1               5                   10                  15

Asp Thr Arg Arg Met Asn Met Phe Val Ser Val Ala Ala Val Ala
            20                  25                  30

Gly Leu Leu Phe Gly Leu Asp Ile Gly Val Ile Ala Gly Ala Leu Pro
        35                  40                  45

Phe Ile Thr Asp His Phe Val Leu Thr Ser Arg Leu Gln Glu Trp Val
    50                  55                  60

Val Ser Ser Met Met Leu Gly Ala Ala Ile Gly Ala Leu Phe Asn Gly
65                  70                  75                  80

Trp Leu Ser Phe Arg Leu Gly Arg Lys Tyr Ser Leu Met Ala Gly Ala
                85                  90                  95

Ile Leu Phe Val Leu Gly Ser Ile Gly Ser Ala Phe Ala Thr Ser Val
            100                 105                 110

Glu Met Leu Ile Ala Ala Arg Val Leu Gly Ile Ala Val Gly Ile
        115                 120                 125

Ala Ser Tyr Thr Ala Pro Leu Tyr Leu Ser Glu Met Ala Ser Glu Asn
    130                 135                 140

Val Arg Gly Lys Met Ile Ser Met Tyr Gln Leu Met Val Thr Leu Gly
145                 150                 155                 160

Ile Val Leu Ala Phe Leu Ser Asp Thr Ala Phe Ser Tyr Ser Gly Asn
                165                 170                 175

Trp Arg Ala Met Leu Gly Val Leu Ala Leu Pro Ala Val Leu Leu Ile
            180                 185                 190
```

```
Ile Leu Val Val Phe Leu Pro Asn Ser Pro Arg Trp Leu Ala Glu Lys
            195                 200                 205

Gly Arg His Ile Glu Ala Glu Val Leu Arg Met Leu Arg Asp Thr
    210                 215                 220

Ser Glu Lys Ala Arg Glu Leu Asn Glu Ile Arg Glu Ser Leu Lys
225                 230                 235                 240

Leu Lys Gln Gly Gly Trp Ala Leu Phe Lys Ile Asn Arg Asn Val Arg
                245                 250                 255

Arg Ala Val Phe Leu Gly Met Leu Leu Gln Ala Met Gln Gln Phe Thr
            260                 265                 270

Gly Met Asn Ile Ile Met Tyr Tyr Ala Pro Arg Ile Phe Lys Met Ala
        275                 280                 285

Gly Phe Thr Thr Thr Glu Gln Gln Met Ile Ala Thr Leu Val Val Gly
        290                 295                 300

Leu Thr Phe Met Phe Ala Thr Phe Ile Ala Val Phe Thr Val Asp Lys
305                 310                 315                 320

Ala Gly Arg Lys Pro Ala Leu Lys Ile Gly Phe Ser Val Met Ala Leu
                325                 330                 335

Gly Thr Leu Val Leu Gly Tyr Cys Leu Met Gln Phe Asp Asn Gly Thr
            340                 345                 350

Ala Ser Ser Gly Leu Ser Trp Leu Ser Val Gly Met Thr Met Met Cys
        355                 360                 365

Ile Ala Gly Tyr Ala Met Ser Ala Ala Pro Val Val Trp Ile Leu Cys
370                 375                 380

Ser Glu Ile Gln Pro Leu Lys Cys Arg Asp Phe Gly Ile Thr Cys Ser
385                 390                 395                 400

Thr Thr Thr Asn Trp Val Ser Asn Met Ile Ile Gly Ala Thr Phe Leu
                405                 410                 415

Thr Leu Leu Asp Ser Ile Gly Ala Ala Gly Thr Phe Trp Leu Tyr Thr
            420                 425                 430

Ala Leu Asn Ile Ala Phe Val Gly Ile Thr Phe Trp Leu Ile Pro Glu
        435                 440                 445

Thr Lys Asn Val Thr Leu Glu His Ile Glu Arg Lys Leu Met Ala Gly
    450                 455                 460

Glu Lys Leu Arg Asn Ile Gly Val
465                 470

<210> SEQ ID NO 3
<211> LENGTH: 180
<212> TYPE: DNA
<213> ORGANISM: Artificial sequence
<220> FEATURE:
<223> OTHER INFORMATION: hybrid promoter

<400> SEQUENCE: 3
ctagatctct cacctaccaa acaatgcccc cctgcaaaaa ataaattcat aaaaaacata      60
cagataacca tctgcggtga taaattatct ctggcggtgt tgacaattaa tcatcggctc    120
gtataatgtg tggaattgtg agcgtcttac tctctgctgg caggaaaaaa tggttactat    180

<210> SEQ ID NO 4
<211> LENGTH: 35
<212> TYPE: DNA
<213> ORGANISM: Artificial sequence
<220> FEATURE:
<223> OTHER INFORMATION: primer
```

<400> SEQUENCE: 4
taagtaagat cttgatgtcc ggcggtgctt ttgcc                                35

<210> SEQ ID NO 5
<211> LENGTH: 57
<212> TYPE: DNA
<213> ORGANISM: Artificial sequence
<220> FEATURE:
<223> OTHER INFORMATION: primer

<400> SEQUENCE: 5
catgtcgcag caatttaatc catatttatg ctgttttac gccccgccct gccactc        57

<210> SEQ ID NO 6
<211> LENGTH: 25
<212> TYPE: DNA
<213> ORGANISM: Artificial sequence
<220> FEATURE:
<223> OTHER INFORMATION: primer

<400> SEQUENCE: 6
atagtaacca tttttcctg ccagc                                           25

<210> SEQ ID NO 7
<211> LENGTH: 26
<212> TYPE: DNA
<213> ORGANISM: Artificial sequence
<220> FEATURE:
<223> OTHER INFORMATION: primer

<400> SEQUENCE: 7
attttatctg ctgtaaaatt aggtgg                                         26

<210> SEQ ID NO 8
<211> LENGTH: 20
<212> TYPE: DNA
<213> ORGANISM: Artificial sequence
<220> FEATURE:
<223> OTHER INFORMATION: primer

<400> SEQUENCE: 8
gtatcccgca aagaacgtgg                                                20

<210> SEQ ID NO 9
<211> LENGTH: 54
<212> TYPE: DNA
<213> ORGANISM: Artificial sequence
<220> FEATURE:
<223> OTHER INFORMATION: primer

<400> SEQUENCE: 9
tttgctttct tctttcaata ccttaacggt atagcgtgaa gcctgctttt ttat          54

<210> SEQ ID NO 10
<211> LENGTH: 54
<212> TYPE: DNA
<213> ORGANISM: Artificial sequence
<220> FEATURE:
<223> OTHER INFORMATION: primer

<400> SEQUENCE: 10
agatatgact atgaacgtta ttgcaatatt gaatcacgct caagttagta taaa          54

<210> SEQ ID NO 11
<211> LENGTH: 54

```
<212> TYPE: DNA
<213> ORGANISM: Artificial sequence
<220> FEATURE:
<223> OTHER INFORMATION: primer

<400> SEQUENCE: 11
ggaggaacac atgaacatca ttgccattat gggacctgaa gcctgctttt ttat            54

<210> SEQ ID NO 12
<211> LENGTH: 53
<212> TYPE: DNA
<213> ORGANISM: Artificial sequence
<220> FEATURE:
<223> OTHER INFORMATION: primer

<400> SEQUENCE: 12
cgccattttt aggactcgta cgcggtaaac gccgtccgtc aagttagtat aaa             53

<210> SEQ ID NO 13
<211> LENGTH: 30
<212> TYPE: DNA
<213> ORGANISM: Artificial sequence
<220> FEATURE:
<223> OTHER INFORMATION: primer

<400> SEQUENCE: 13
ccgacctggt acctgcgtga gttgttcacg                                       30

<210> SEQ ID NO 14
<211> LENGTH: 30
<212> TYPE: DNA
<213> ORGANISM: Artificial sequence
<220> FEATURE:
<223> OTHER INFORMATION: primer

<400> SEQUENCE: 14
aaaagggccg gagctccagc acatccggcc                                       30
```